(12) United States Patent
Zhang et al.

(10) Patent No.: US 7,759,331 B2
(45) Date of Patent: Jul. 20, 2010

(54) PYRIDINE-CONTAINING MACROHETEROCYLIC COMPOUNDS AS KINASE INHIBITORS

(75) Inventors: Han-Cheng Zhang, Lansdale, PA (US); Llorente Vincente R. Bonaga, Santa Clara, CA (US); Claudia K. Derian, Hatboro, PA (US); Bruce E. Maryanoff, Forest Grove, PA (US); Hong Ye, Lansdale, PA (US)

(73) Assignee: Janssen Pharmaceutica NV (BE)

( * ) Notice: Subject to any disclaimer, the term of this patent is extended or adjusted under 35 U.S.C. 154(b) by 27 days.

(21) Appl. No.: 11/716,185

(22) Filed: Mar. 9, 2007

(65) Prior Publication Data

US 2007/0213352 A1 Sep. 13, 2007

Related U.S. Application Data

(60) Provisional application No. 60/781,120, filed on Mar. 10, 2006.

(51) Int. Cl.
| | | |
|---|---|---|
| A01N 43/00 | (2006.01) | |
| A61K 31/33 | (2006.01) | |
| C07D 225/00 | (2006.01) | |
| C07D 295/00 | (2006.01) | |

(52) U.S. Cl. ...................... 514/183; 540/450
(58) Field of Classification Search ........................ None
See application file for complete search history.

(56) References Cited

U.S. PATENT DOCUMENTS

| 4,513,006 | A | 4/1985 | Maryanoff et al. | |
|---|---|---|---|---|
| 5,624,949 | A | 4/1997 | Heath et al. | |
| 6,828,327 | B2 | 12/2004 | Kuo et al. | |
| 7,067,507 | B2 * | 6/2006 | Pulley et al. | 514/183 |

FOREIGN PATENT DOCUMENTS

EP 0 657 458 8/2001

OTHER PUBLICATIONS

"Substructure search", http://www.sigmaaldrich.com/catalog/search/substructure/SubstructureSearchPage, accessed Dec. 12, 2008.*
Zhang et al. Bioorganic and Medicinal Chemistry, 2007, 17, 2863-68.*
Eldar-Finkelman et al. Expert Opinion in Therapeutic Targets, 2006, 10(2), 199-201.*
Kannoji et al. Expert Opinion in Therapeutic Targets, 2008, 12(11), 1443-55.*
"Inflammation", http://www.nlm.nih.gov/cgi/mesh/2008/MB_cgi, accessed Dec. 12, 2008.*
"Skin Diseases", http://www.nlm.nih.gov/cgi/mesh/2008/MB_cgi?mode=&term=Skin+Diseases, accessed Dec. 12, 2008.*
"Central Nervous System Diseases", http://www.nlm.nih.gov/cgi/mesh/2008/MB_cgi, accessed Dec. 12, 2008.*
"Bipolar Disorder-Prevention", http://www.webmd.com/bipolar-disorder/tc/bipolar-disorder-prevention, accessed Dec. 12, 2008.*
"Schizophrenia-Prevention", http://www.webmd.com/schizophrenia/tc/schizophrenia-prevention, accessed Dec. 12, 2008.*
"Type 1 Diabetes-Prevention", http://diabetes.webmd.com/tc/type-1-diabetes-prevention, accessed Dec. 12, 2008.*
"Type 2 Diabetes-Prevention", http://diabetes.webmd.com/tc/type-2-diabetes-prevention, accessed Dec. 12, 2008.*
Shen et al. Bioorganic and Medicinal Chemistry, 2004, 12, 1239-55.*
Embi, et al., "Glycogen Synthase Kinase-3 from Rabbit Skeletal Muscle Separation from Cyclic-AMP-Dependent Protein Kinase and Phosphorylase Kinase", Eur. J. Biochem, 1980, vol. 107, pp. 519-527.
Cross, et al., "The Inhibition of glycogen synthase kinase-3 by insulin or insulin-like growth factor 1 in the rat skeletal muscle cell line L6 is blocked by wortmannin, blocks activation of the mitogen-activated protein kinase pathway in L6 cells between Ras and Rat", Biochemical Journal, 1994, vol. 303, pp. 21-26.
Villar-Palasi, et al., "Insulin-mediated effect on the activity of UDPG-glycogen transglucosylase of muscle", Biochim. Biophys. Acta, 1960, vol. 39, pp. 171-173.
Parker, et. al., "Glycogen Synthase from Rabbit Skeletal Muscle; Effect of Insulin on the State of Phosphorylatio of the Seven Phosphoserine residues in vivo", Eur. J. Biochem, 1983, vol. 130, pp. 227-234.
Cohen, " Dissection of the Protein Phosphorylation Cascades Involved in Insulin and Growth Factor Action", Biochem. Soc. Trans., 1993, vol. 21, pp. 555-567.
Srivastava, et al., "Potential mechanism(s) involved in the regulation of glycogen synthesis by insulin", Mol. And Cellular Biochem, 1998, vol. 182, pp. 135-141.
Chen, et al., "Sequence of the Human Glycogen-Associated Regulatory Subunit of Type 1 Protein Phosphatase and Analysis of Its Coding region and mRNA Level in Muscle From Patients with NIDDM", Diabetes, 1994, vol. 43, pp. 1234-1241.
Eldar-Findelman, et al., " Phosphorylation of insulin receptor substrate 1 by glycogen synthase kinase 3 impairs insulin action", 1997, vol. 94, pp. 9660-9664.
Eldar-Finkelman, et al., "Increased Glycogen Synthase Kinase-3 Activity in Diabetes-and Obesity-Prone C57BL/6J Mice", Diabetes, 1999, vol., 48, pp. 1662-1666.
Hoeflich, et al., "Requirement for glycogen synthase kinase-3β in cell survival and NF-kB activation", Nature, vol. 406, 2000, pp. 86-90.
Gat, et al., "De Novo Hair Expressing a Truncated β-Catenin in Skin", Cell, 1998, vol. 95, pp. 605-614.
Pap, et al., "Role of Glycogen Synthase Kinase-3 in the Phosphatidylinositol 3-Kinase/Akt Cell Survival Pathway", J. Biol. Chem., 1998, vol. 273, pp. 19929-19932.
D'Mello, et al, "Lithium Induces Apoptosis in Immature Cerebellar granule cells but Promotes Survival of Mature Neurons", Exp. Cell Res., 1994, vol. 211, pp. 332-338.

(Continued)

*Primary Examiner*—James O Wilson
*Assistant Examiner*—Noble Jarrell
(74) *Attorney, Agent, or Firm*—Yuriy P. Stercho

(57) ABSTRACT

This invention is directed to pyridine-containing macroheterocyclic compounds useful as kinase inhibitors, methods for producing such compounds and methods for treating or preventing a kinase mediated disorder.

34 Claims, No Drawings

OTHER PUBLICATIONS

Nonaka, et al., "Neuroprotective effects of chronic lithium on focal cerebral ischemia in rats", Neuroreport, 1998, vol. 9(9), pp. 2081-2084.

Hong, et al., "Lithium reduces Tau Phosphorylation by Inhibition of glycogen Synthase Kinase-3*", J. Biol. Chem., 1997, vol. 272(40), pp. 25326-25332.

Ikeda, et al. "Axin, a negative regulator of the Wnt signaling pathway, forms a complex with GSK-3β-catenin", EMBO J., 1998, vol. 17, pp. 1371-1384.

Cotter, et al. "Abnormalities of Wnt signaling in schizophrenia-evidence for neurodevelopmental abnormality", Neuroreport, 1998, vol. 9, pp. 1379-1383.

Manjii, et al., "", J. Clin. Psychiatry, 1999, vol. 60 Suppl 2, pp. 27-39.

Davies, et al. "Specificity and mechanism of action of some commonly used protein kinase inhibitors" Biochem. J. 2000, vol. 351, pp. 95-105.

Zhang, et al. "Novel bis(indolyl)maleimide pyridinophanes that are potent, selective inhibitors of glycogen synthase kinase-3", Biorganic & Medicinal Chemistry Letters, vol. 17, 2007, pp. 2863-2868.

Kannoji, "GSK3β: a master switch and a promising target", Expert Opinion, Ther, Targets, 2008, vol. 12 (11), pp. 1443-1455.

Greene, T.W., et al., "Protective groups in Organic Chemistry," John Wiley & Sons, Inc., 1991, pp. 105-106.

* cited by examiner

PYRIDINE-CONTAINING MACROHETEROCOCYLIC COMPOUNDS AS KINASE INHIBITORS

CROSS-REFERENCE TO RELATED APPLICATIONS

This present application claims benefit of U.S. Provisional Patent Application Ser. No. 60/781,120, filed Mar. 10, 2006, which is incorporated herein by reference in its entirety and for all purposes.

FIELD OF THE INVENTION

This invention is directed to certain novel pyridine-containing macroheterocyclic compounds, methods for preparing such compounds, and methods for treating or preventing a kinase mediated disorder. More particularly, this invention is directed to macrocyclic 1H-indole and 1H-pyrrolo[2,3-b]pyridine compounds useful as selective kinase inhibitors, methods for producing such compounds and methods for treating or preventing a kinase mediated disorder.

BACKGROUND OF THE INVENTION

U.S. Pat. No. 5,624,949 to Heath, Jr., et. al., describes bis-indolemaleimide derivatives as PKC inhibitors and as selective PKCβ-I and PKCβ-II inhibitors, but does not disclose or suggest the compounds of the present invention.

U.S. Pat. No. 6,828,327 to Kuo et. al., describes macrocyclic compounds useful as kinase inhibitors, but does not disclose or suggest the compounds of the present invention.

European patent application EP 657458 A1 to Jirousek, M. et. al. describes bis(indolyl)maleimide macrocycles as β-isoenzyme selective protein kinase C inhibitors, but does not disclose or suggest the compounds of the present invention.

SUMMARY OF THE INVENTION

The present invention provides a macroheterocyclic compound of Formula (I):

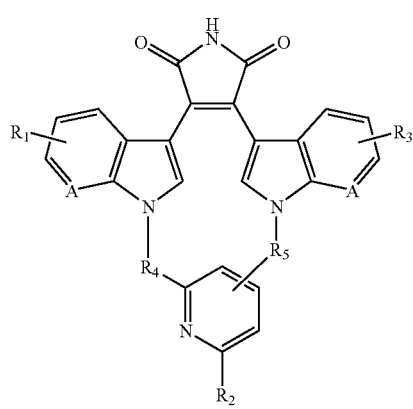

Formula (I)

wherein

A is CH or N, to form 1H-indole or 1H-pyrrolo[2,3-b]pyridine, respectively;

$R_1$ and $R_3$ are each selected from the group consisting of hydrogen, $C_{1-4}$alkyl, $C_{2-4}$alkenyl, $C_{1-4}$alkoxy, $C_{1-4}$alkylthio, halogen, trifluoromethyl, trifluoromethoxy, hydroxy, hydroxy($C_{1-4}$)alkyl, nitro, amino, ($C_{1-4}$)alkylamino, and di($C_{1-4}$)alkylamino;

$R_4$ and $R_5$ are each $C_{2-6}$alkylene optionally substituted with oxo, wherein the point of attachment for $R_5$ is meta or ortho relative to the $R_2$ substituted pyridine carbon ring atom of the compound of Formula (I);

$R_2$ is $C_{6-10}$aryl or $NR_aR_b$; wherein $C_{10}$aryl is optionally substituted with one, two or three substituents independently selected from the group consisting of $C_{1-4}$alkyl, $C_{1-4}$alkoxy, halogen, amino, ($C_{1-4}$)alkylamino, di($C_{1-4}$)alkylamino, and $C_{1-4}$alkoxycarbonyl;

$R_a$ and $R_b$ are each $C_{1-6}$alkyl; or, $R_a$ and $R_b$ are taken together with the atoms to which they are attached to form a 5, 6, 7 or 8 membered monocyclic ring;

wherein said monocyclic ring optionally contains one additional oxygen, sulfur, NH, or N($C_{1-4}$alkyl);

and enantiomers, diastereomers, racemates, and pharmaceutically acceptable salts thereof.

The present invention is directed to pyridine-containing macroheterocyclic compounds useful as a selective kinase inhibitor. The present invention is further directed to compounds useful as inhibitors of glycogen synthase kinase-3. The present invention is further directed to compounds useful as inhibitors of glycogen synthase kinase-3β.

The present invention is also directed to methods for producing the instant pyridine-containing macroheterocyclic compounds and pharmaceutical compositions and medicaments containing such compounds.

The present invention is further directed to methods for treating or preventing a kinase mediated disorder. In particular, the method of the present invention is directed to treating or preventing a kinase-mediated disorder such as, but not limited to, diabetes, inflammatory diseases, dermatological disorders, and CNS (central nervous system) disorders such as schizophrenia, bipolar disorder, manic depression, and Alzheimer's disease.

The present invention is also directed to a process for synthesizing pyridine-containing macrocycle compounds of Formula (I) using a cobalt-mediated [2+2+2] co-cyclotrimerization.

DETAILED DESCRIPTION OF THE INVENTION

As used herein, with reference to substituents, the term "independently" means that when more than one of such substituent is possible, such substituents may be the same or different from each other.

Chemical Definitions

As used herein, the following terms are intended to have the following meanings (additional definitions are provided where needed throughout the Specification).

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, "alkyl" whether used alone or as part of a substituent group refers to straight and branched carbon chain hydrocarbon alkyl radical, having 1 to 8 carbon atoms or any number within this range. Examples include methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl and the like. Other examples include $C_{1-4}$alkyl groups. Alkyl is optionally substituted on one or more available carbon chain atoms with one or more substituents when allowed by available valences.

Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, the term "alkylene" refers to an alkyl group, as defined herein, which functions as a linking group.

As used herein, unless otherwise noted, the term "alkoxy" refers to a straight or branched chain hydrocarbon alkyl radical of the formula —O-alkyl, wherein alkyl is as defined supra. Examples include methoxy, ethoxy, propoxy and the like. Other examples include $C_{1-4}$alkoxy groups. Alkoxy is optionally substituted on one or more available carbon chain atoms with one or more substituents when allowed by available valences.

Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. Examples include ethenyl, ethynyl, allyl and the like. Other examples include $C_{2-4}$alkenyl or $C_{2-4}$alkynyl groups. Alkenyl and alkynyl are optionally substituted on one or more available carbon chain atoms with one or more substituents when allowed by available valences.

The term "cycloalkyl" refers to saturated or partially unsaturated, monocyclic or polycyclic hydrocarbon rings of from 3 to 14 carbon atom members. Examples of such rings include, and are not limited to cyclopropyl, cyclobutyl, cyclopentyl, cyclohexyl, cycloheptyl, cyclooctyl, indanyl, indenyl and adamantyl. Alternatively, the cycloalkyl ring may be fused to a benzene ring (benzo fused cycloalkyl), a 5 or 6 membered heteroaryl ring (containing one of O, S or N and, optionally, one additional nitrogen) to form a heteroaryl fused cycloalkyl. A cycloalkyl ring is optionally substituted on one or more available ring carbon atoms with one or more substituents when allowed by available valences.

The term "heterocyclyl" refers to a nonaromatic (saturated or partially unsaturated) monocyclic or polycyclic ring of 5 to 7 members in which 1 to 2 members are nitrogen, or a nonaromatic monocyclic or polycyclic ring of 5 to 7 members in which zero, one or two members are nitrogen and up to two members are oxygen or sulfur; wherein, optionally, the ring contains zero to one unsaturated bonds, and, optionally, when the ring is of 6 or 7 members, it contains up to two unsaturated bonds. A heterocyclyl ring is optionally substituted on one or more available ring atoms with one or more substituents when allowed by available valences.

The term "heterocyclyl" includes a 5 to 7 membered saturated or partially unsaturated monocyclic or polycyclic heterocyclic ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety.

For instant compounds of the invention, the carbon atom ring members that form the heterocyclyl ring are fully saturated. Other compounds of the invention may have a partially saturated heterocyclyl ring. The term "heterocyclyl" also includes a 5 to 7 membered monocyclic heterocycle bridged to form bicyclic rings. Such compounds are not considered to be fully aromatic and are not referred to as heteroaryl compounds.

Examples of heterocyclyl groups include, and are not limited to, pyrrolinyl (including 2H-pyrrole, 2-pyrrolinyl or 3-pyrrolinyl), pyrrolidinyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, morpholinyl, thiomorpholinyl, piperazinyl, 1,3-dioxolanyl, 1,4-dioxanyl, 1,4-dithianyl, azetidinyl, azepanyl, azepinyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like.

Examples of benzofused-heterocyclyl ring system radicals include, and are not limited to, indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl and the like.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, biphenyl, naphthalenyl, azulenyl or anthracenyl. phenyl, biphenyl, naphthalene (also referred to as naphthalenyl and naphthyl), azulenyl, anthracenyl and the like. A cycloalkyl ring is optionally substituted on one or more available ring carbon atoms with one or more substituents when allowed by available valences.

The term "heteroaryl" refers to an unsaturated, aromatic monocyclic or polycyclic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has, three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Heteroaryl radicals may be attached to a core molecule and further substituted on any atom when allowed by available valences.

The term "benzofused," when used as a prefix for a ring system, refers to a radical formed by any monocyclic radical fused with a benzene ring; the benzofused radical may be attached to a core molecule via either ring of the bicyclic system.

Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; examples of benzofused heteroaryl groups include indolyl, indolizinyl, azaindolyl, isoindolyl, indolinyl, benzofuryl, benzothienyl, indazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, cinnolinyl, phthalzinyl, quinoxalinyl, 1,8-naphthyridinyl, pteridinyl or quinazolinyl. Benzofused-heteroaryl radicals may be attached to a core molecule and further substituted on any atom when allowed by available valences.

The terms "halogen" and "halo" refer to fluorine, chlorine, bromine and iodine. Substituents that are substituted with multiple halogens are substituted in a manner that provides compounds which are stable.

Compounds of Formula (I) were named according to the following numbering conventions:

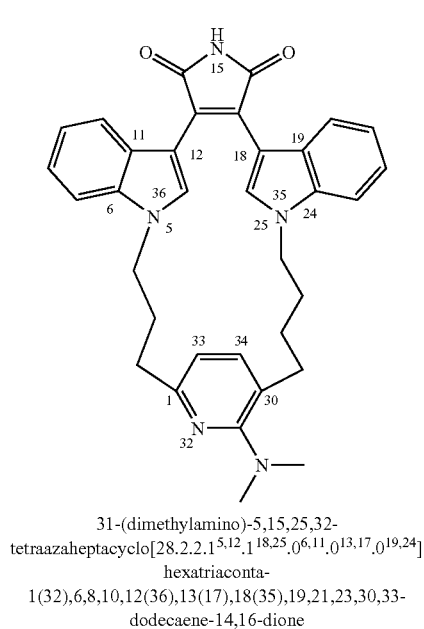

Cpd 1

31-(dimethylamino)-5,15,25,32-
tetraazaheptacyclo[28.2.2.1$^{5,12}$.1$^{18,25}$.0$^{6,11}$.0$^{13,17}$.0$^{19,24}$]
hexatriaconta-
1(32),6,8,10,12(36),13(17),18(35),19,21,23,30,33-
dodecaene-14,16-dione

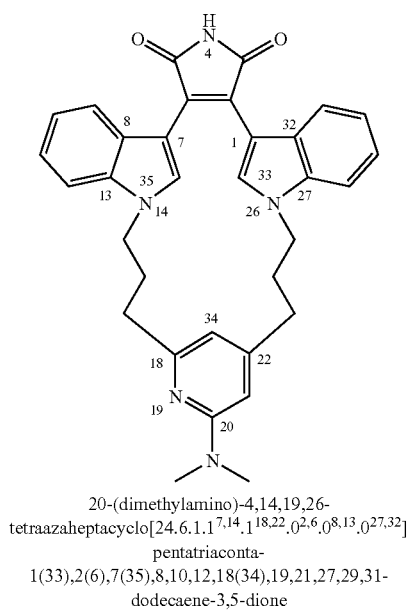

Cpd 2

20-(dimethylamino)-4,14,19,26-
tetraazaheptacyclo[24.6.1.1$^{7,14}$.1$^{18,22}$.0$^{2,6}$.0$^{8,13}$.0$^{27,32}$]
pentatriaconta-
1(33),2(6),7(35),8,10,12,18(34),19,21,27,29,31-
dodecaene-3,5-dione

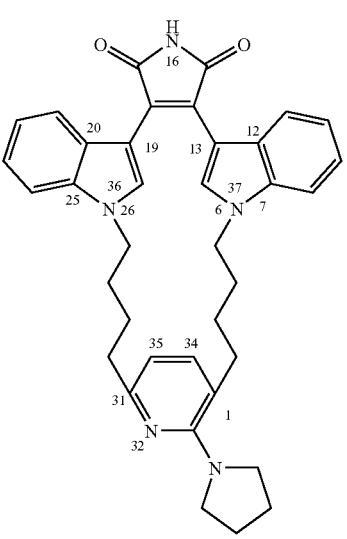

Cpd 5

33-pyrrolidin-1-yl-6,16,26,32-
tetraazaheptacyclo[29.2.2.1$^{6,13}$.1$^{19,26}$.0$^{7,12}$.0$^{14,18}$.0$^{20,25}$]
heptatriaconta-
1(33),7,9,11,13(37),14(18),19(36),20,22,24,31,34-
dodecaene-15,17-dione In general, the nomenclature rules for substituents used throughout this disclosure describe the terminal portion of the designated side chain first followed by the adjacent functionality toward the point of attachment. Thus, for example, a "phenylC$_1$-C$_6$ alkylamidoC$_1$-C$_6$alkyl" substituent refers to a group of the formula:

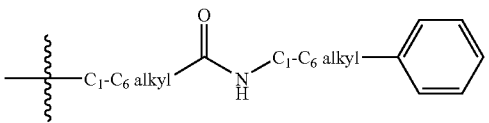

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, unless otherwise noted, the term "aprotic organic solvent" shall mean any solvent that does not yield a proton. Suitable examples include, but are not limited to DMF, dioxane, THF, acetonitrile, pyridine, dichloroethane, dichloromethane, dimethoxyethane, MTBE, toluene, and the like.

Embodiments of the present invention include compounds of Formula (I) wherein:
(a) A is CH such that the A-containing ring system of Formula (I) is 1H-indole;
(b) $R_1$ and $R_3$ are each selected from the group consisting of hydrogen, methyl, methoxy, halogen, and hydroxy;
(c) $R_1$ and $R_3$ are each hydrogen;
(d) $R_4$ and $R_5$ are each $C_{3-4}$alkylene, wherein the point of attachment for $R_5$ is meta or ortho relative to the $R_2$ substituted pyridine carbon ring atom of the compound of Formula (I);
(e) $R_4$ and $R_5$ are each n-propylene or n-butylene;
(f) $R_2$ is $C_{6-10}$aryl or $NR_aR_b$; wherein $C_{6-10}$aryl is optionally substituted with one or two substituents independently selected from the group consisting of $C_{1-4}$alkyl and halogen;
(g) $R_2$ is phenyl is optionally substituted with one to two methyl substituents;
(h) $R_2$ is phenyl optionally substituted with one methyl substituent;
(i) $R_2$ is 4-methyl-phenyl;
(j) $R_a$ and $R_b$ are each $C_{1-4}$alkyl; or $R_a$ and $R_b$ are taken together with the atoms to which they are attached to form a 5 to 6 membered monocyclic ring; and
(k) $R_a$ and $R_b$ are each $C_{1-2}$alkyl; or $R_a$ and $R_b$ are taken together with the atoms to which they are attached to form a 5-membered monocyclic ring.

A further embodiment of the present invention is directed to a compound of Formula (Ia):

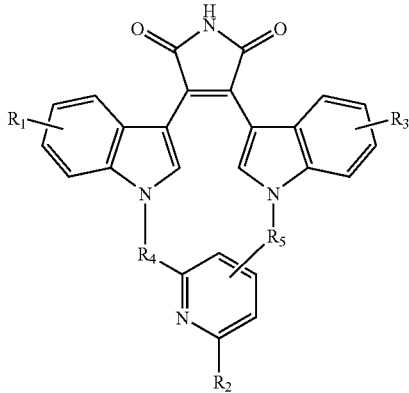

Formula (Ia)

wherein:
$R_1$ and $R_3$ are each selected from the group consisting of hydrogen, methyl, methoxy, halogen, and hydroxy;
$R_4$ and $R_5$ are each $C_{3-4}$alkylene, wherein the point of attachment for $R_5$ is meta or ortho relative to the $R_2$ substituted pyridine carbon ring atom of the compound of Formula (I);
$R_2$ is $C_{6-10}$aryl or $NR_aR_b$; wherein $C_{6-10}$aryl is optionally substituted with one, two or three substituents independently selected from the group consisting of $C_{1-4}$alkyl and halogen;

$R_a$ and $R_b$ are each $C_{1-4}$alkyl; or $R_a$ and $R_b$ are taken together with the atoms to which they are attached to form a 5 to 6 membered monocyclic ring;
and enantiomers, diastereomers, racemates, and pharmaceutically acceptable salts thereof.

A further embodiment of the present invention is directed to a compound of Formula (Ia) wherein:
$R_1$ and $R_3$ are each hydrogen; and
$R_2$ is $C_{6-10}$aryl or $NR_aR_b$; wherein $C_{6-10}$aryl is optionally substituted with one or two substituents independently selected from the group consisting of $C_{1-4}$alkyl and halogen.

A further embodiment of the present invention is directed to a compound of Formula (Ia) wherein:
$R_4$ and $R_5$ are each n-propylene or n-butylene;
$R_2$ is phenyl or $NR_aR_b$; wherein phenyl is optionally substituted with one to two methyl substituents; and
$R_a$ and $R_b$ are each $C_{1-2}$alkyl; or $R_a$ and $R_b$ are taken together with the atoms to which they are attached to form a 5-membered monocyclic ring.

A further embodiment of the present invention is directed to compositions comprising a compound of Formula (Ia) wherein $R_2$ is 4-methyl-phenyl or $NR_aR_b$.

A representative compound of Formula (I) or a form thereof includes a compound selected from the group consisting of:

| Cpd | Name |
|---|---|
| 1 | 31-(dimethylamino)-5,15,25,32-tetraazaheptacyclo[28.2.2.1$^{5,12}$.1$^{18,25}$.0$^{6,11}$.0$^{13,17}$.0$^{19,24}$]hexatriaconta-1(32),6,8,10,12(36),13(17),18(35),19,21,23,30,33-dodecaene-14,16-dione, |
| 2 | 20-(dimethylamino)-4,14,19,26-tetraazaheptacyclo[24.6.1.1$^{7,14}$.1$^{18,22}$.0$^{2,6}$.0$^{8,13}$.0$^{27,32}$]pentatriaconta-1(33),2(6),7(35),8,10,12,18(34),19,21,27,29,31-dodecaene-3,5-dione, |
| 3 | 31-(dimethylamino)-5,15,25,30-tetraazaheptacyclo[27.2.2.1$^{5,12}$.1$^{18,25}$.0$^{6,11}$.0$^{13,17}$.0$^{19,24}$]pentatriaconta-1(31),6,8,10,12(35),13(17),18(34),19,21,23,29,32-dodecaene-14,16-dione, |
| 4 | 20-(4-methylphenyl)-4,14,19,26-tetraazaheptacyclo[24.6.1.1$^{7,14}$.1$^{18,22}$.0$^{2,6}$.0$^{8,13}$.0$^{27,32}$]pentatriaconta-1(33),2(6),7(35),8,10,12,18(34),19,21,27,29,31-dodecaene-3,5-dione, |
| 5 | 33-pyrrolidin-1-yl-6,16,26,32-tetraazaheptacyclo[29.2.2.1$^{6,13}$.1$^{19,26}$.0$^{7,12}$.0$^{14,18}$.0$^{20,25}$]heptatriaconta-1(33),7,9,11,13(37),14(18),19(36),20,22,24,31,34-dodecaene-15,17-dione, |
| 6 | 20-pyrrolidin-1-yl-4,14,19,26-tetraazaheptacyclo[24.6.1.1$^{7,14}$.1$^{18,22}$.0$^{2,6}$.0$^{8,13}$.0$^{27,32}$]pentatriaconta-1(33),2(6),7(35),8,10,12,18(34),19,21,27,29,31-dodecaene-3,5-dione, and |
| 7 | 31-pyrrolidin-1-yl-5,15,25,30-tetraazaheptacyclo[27.2.2.1$^{5,12}$.1$^{18,25}$.0$^{6,11}$.0$^{13,17}$.0$^{19,24}$]pentatriaconta-1(31),6,8,10,12(35),13(17),18(34),19,21,23,29,32-dodecaene-14,16-dione. |

Embodiments of the present invention include compounds selected from the group consisting of:
Cpd 1
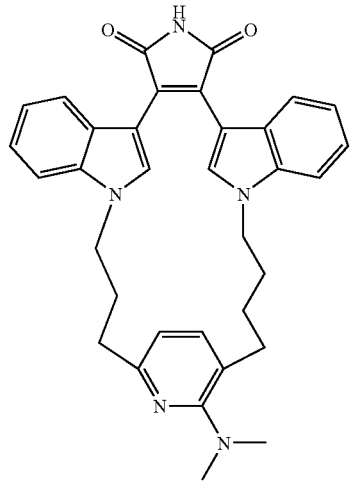
Cpd 2
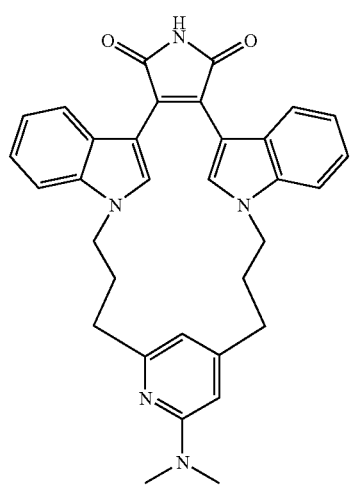
Cpd 3
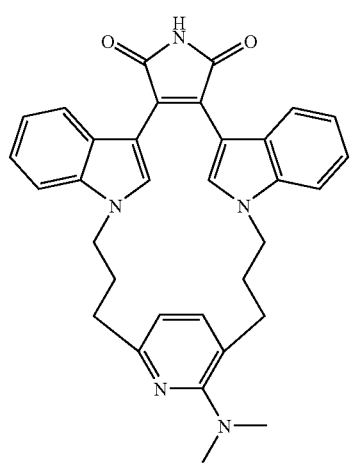
Cpd 4
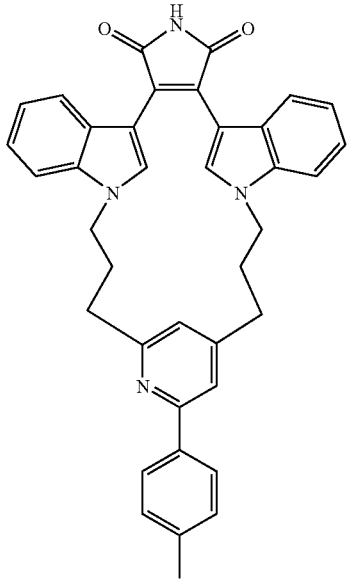
Cpd 5
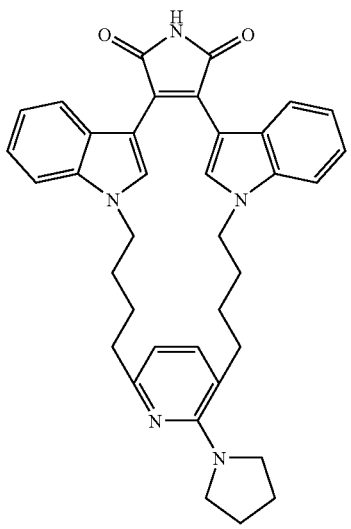
Cpd 6
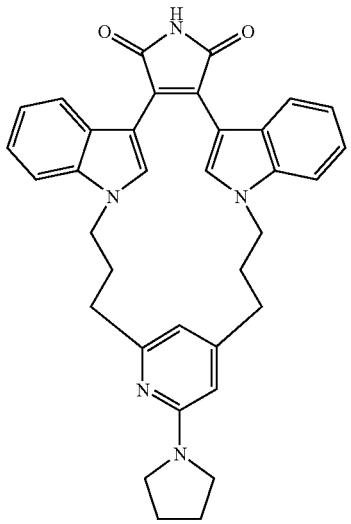

-continued

Cpd 7

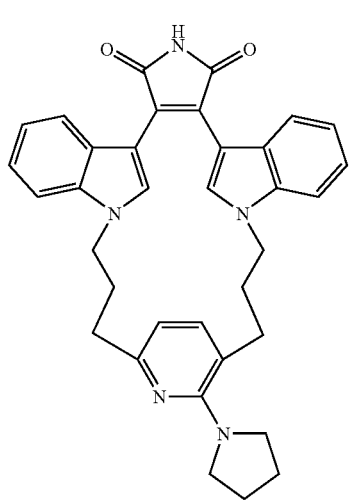

Illustrative of the invention is a pharmaceutical composition comprising a pharmaceutically acceptable carrier and a compound of Formula (I). An illustration of the invention is a pharmaceutical composition made by mixing a compound of Formula (I) and a pharmaceutically acceptable carrier.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicine, the "pharmaceutically acceptable salts" of the compounds of this invention refer to non-toxic acidic/anionic or basic/cationic salt forms. Other salts may, however, be useful in the preparation of compounds according to this invention or of their pharmaceutically acceptable salts.

Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid, adipic acid, glycolic acid, malonic acid, saccharinic acid, trifluoroacetic acid or phosphoric acid.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include the following: acetate, adipate, benzenesulfonate, benzoate, bicarbonate, bisulfate, bitartrate, borate, bromide, calcium, calcium edetate, camsylate (or camphosulphonate), carbonate, chloride, clavulanate, citrate, dihydrochloride, edetate, edisylate, estolate, esylate, fumarate, gluceptate, gluconate, glutamate, glycollylarsanilate, glyconate, hexylresorcinate, hydrabamine, hydrobromide, hydrochloride, hydroxynaphthoate, iodide, isothionate, lactate, lactobionate, laurate, malate, maleate, malonate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, saccharinate, salicylate, stearate, sulfate, subacetate, succinate, tannate, tartrate, teoclate, tosylate, trichloroacetate, triethiodide and valerate.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Furthermore, some of the crystalline forms for the compounds may exist as polymorphs or amorphous crystalline forms and as such are intended to be included in the present invention. In addition, some of the compounds may form solvates with water (i.e., hydrates) or common organic solvents (e.g., organic esters such as ethanolate and the like), and such solvates are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art. The scope of the present invention encompasses all such protected compound forms and mixtures thereof.

Even though the compounds of the present invention (including their pharmaceutically acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. There can, of course, be individual instances where higher or lower dosage ranges are merited, and such are within the scope of this invention.

The invention also provides a pharmaceutical or veterinary pack or kit comprising one or more containers filled with one or more of the ingredients of the pharmaceutical and veterinary compositions of the invention.

Glycogen Synthase Kinase-3

Glycogen synthase kinase-3 (GSK-3) is a serine/threonine protein kinase composed of two isoforms ($\alpha$ and $\beta$) which are encoded by distinct genes. GSK-3 is one of several protein kinases which phosphorylate glycogen synthase (GS) (Embi, et al., *Eur. J. Biochem*, 1980, 107, 519-527). The $\alpha$ and $\beta$ isoforms have a monomeric structure of 49 and 47 kD respectively and are both found in mammalian cells. Both isoforms phosphorylate muscle glycogen synthase (Cross, et al., *Biochemical Journal*, 1994, 303, 21-26) and these two isoforms show good homology between species (human and rabbit GSK-3$\alpha$ are 96% identical).

Diabetes

Type II diabetes (or Non-Insulin Dependent Diabetes Mellitus, NIDDM) is a multifactorial disease. Hyperglycemia is due to insulin resistance in the liver, muscle and other tissues coupled with inadequate or defective secretion of insulin from pancreatic islets. Skeletal muscle is the major site for insulin-stimulated glucose uptake. In this tissue, glucose removed from the circulation is either metabolised through glycolysis and the TCA (tricarboxylic acid) cycle or stored as glycogen. Muscle glycogen deposition plays the more important role in glucose homeostasis and Type II diabetic subjects have defective muscle glycogen storage. The stimulation of glycogen synthesis by insulin in skeletal muscle results from the dephosphorylation and activation of glycogen synthase (Villar-Palasi C. and Lamer J., *Biochim. Biophys. Acta*, 1960, 39, 171-173, Parker P. J., et al., *Eur. J. Biochem.*, 1983, 130, 227-234, and Cohen P., *Biochem. Soc. Trans.*, 1993, 21, 555-567). The phosphorylation and dephosphorylation of GS are mediated by specific kinases and phosphatases. GSK-3 is responsible for phosphorylation and deactivation of GS, while glycogen bound protein phosphatase 1 (PP1 G) dephosphorylates and activates GS. Insulin both inactivates GSK-3 and activates PP1G (Srivastava A. K. and Pandey S. K., *Mol. and Cellular Biochem.*, 1998, 182, 135-141).

Studies suggest that an increase in GSK-3 activity might be important in Type II diabetic muscle (Chen, et al., *Diabetes*, 1994, 43, 1234-1241). Overexpression of GSK-3$\alpha$ and constitutively active GSK-3$\beta$ (S9A, S9e) mutants in HEK-293 cells resulted in suppression of glycogen synthase activity (Eldar-Finkelman, et al., *PNAS*, 1996, 93, 10228-10233) and overexpression of GSK-3$\beta$ in CHO cells, expressing both insulin receptor and insulin receptor substrate 1 (IRS-1) resulted in impairment of insulin action (Eldar-Finkelman and Krebs, *PNAS*, 1997, 94, 9660-9664). Recent evidence for the involvement of elevated GSK-3 activity and the development of insulin resistance and Type II diabetes in adipose tissue has emerged from studies undertaken in diabetes and obesity prone C57BL/6J mice (Eldar-Finkelman, et al., *Diabetes*, 1999, 48, 1662-1666).

Inflammatory Diseases

Studies on fibroblasts from the GSK-3$\beta$ knockout mouse indicate that inhibition of GSK-3 may be useful in treating inflammatory disorders or diseases through the negative regulation of NFkB activity (Hoeflich K. P., et al., *Nature,* 2000, 406, 86-90).

Dermatological Disorders

The finding that transient β-catenin stabilization may play a role in hair development (Gat, et al., *Cell,* 1998, 95, 605-614) suggests that GSK-3 inhibitors could also be used in the treatment of baldness.

Central Nervous System Disorders

In addition to modulation of glycogen synthase activity, GSK-3 also plays an important role in the CNS disorders. GSK-3 inhibitors may be of value as neuroprotectants in the treatment of acute stroke and other neurotraumatic injuries (Pap and Cooper, *J. Biol. Chem.,* 1998, 273, 19929-19932). Lithium, a low mM inhibitor of GSK-3, has been shown to protect cerebellar granule neurons from death (D'Mello, et al., *Exp. Cell Res.,* 1994, 211, 332-338) and chronic lithium treatment has demonstrable efficacy in the middle cerebral artery occlusion model of stroke in rodents (Nonaka and Chuang, *Neuroreport,* 1998, 9(9), 2081-2084).

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease and is postulated to promote microtubule disassembly. Lithium has been reported to reduce the phosphorylation of tau, enhance the binding of tau to microtubules and promote microtubule assembly through direct and reversible inhibition of GSK-3 (Hong M. et al *J. Biol. Chem.,* 1997, 272(40), 25326-32). β-catenin is phosphorylated by GSK-3 as part of a tripartite axin protein complex resulting in β-catenin degradation (Ikeda, et al., *EMBO J.,* 1998, 17, 1371-1384). Inhibition of GSK-3 activity is involved in the stabilization of catenin and promotes β-catenin-LEF-1/TCF transcriptional activity (Eastman, Grosschedl, *Curr. Opin. Cell Biol.,* 1999, 11, 233). Studies have also suggested that GSK-3 inhibitors may also be of value in the treatment of schizophrenia (Cotter D., et al. *Neuroreport,* 1998, 9, 1379-1383; Lijam N., et al., *Cell,* 1997, 90, 895-905) and manic depression, also known as bipolar disorder (Manji, et al., *J. Clin. Psychiatry,* 1999, 60, (Suppl 2)27-39 for review).

Accordingly, compounds found useful as GSK-3 inhibitors could have further therapeutic utility in the treatment of diabetes, inflammatory diseases, dermatological disorders and central nervous system disorders.

An embodiment of the present invention is a method for treating or preventing a kinase mediated disorder in a subject in need thereof comprising administering to the subject a therapeutically effective amount of any of the compounds or pharmaceutical compositions of the present invention.

The therapeutically effective amount of the compounds of Formula (I) exemplified in such a method is from about 0.001 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day for an average (70 kg) human; although, it is apparent to one skilled in the art that the therapeutically effective amount for active compounds of the invention will vary as will the conditions being treated.

Embodiments of the present invention include the use of a compound of Formula (I) for the preparation of a medicament for treating or ameliorating a kinase mediated disorder in a subject in need thereof.

A further embodiment of the present invention includes the use of a compound of Formula (I) for the preparation of a medicament for treating or ameliorating a disorder selected from the group consisting of diabetes, inflammatory diseases, dermatological disorders, and CNS (central nervous system) disorders such as schizophrenia, manic depression, and Alzheimer's disease.

The present invention includes a method for treating a kinase mediated disorder. More particularly, the present invention includes a method for inhibiting glycogen synthase kinase-3, and more particularly, for inhibiting glycogen synthase kinase-3β.

An embodiment of the present invention is a method for treating a condition or disorder selected from the group consisting of diabetes, inflammatory diseases, dermatological disorders, and a CNS (central nervous system) disorder selected from the group consisting of schizophrenia, bipolar disorder, and Alzheimer's disease comprising administering to a subject in need of such treatment a therapeutically effective amount of any of the compounds or pharmaceutical compositions of the present invention.

Embodiments of the present invention include a compound or pharmaceutical composition thereof advantageously co-administered in combination with other agents for treating, reducing or ameliorating the effects of a kinase mediated disorder. For example, in the treatment of diabetes, especially Type II diabetes, a compound of Formula (I) or pharmaceutical composition thereof may be used in combination with other agents, especially insulin or antidiabetic agents including, but not limited to, insulin secretagogues (such as sulphonylureas), insulin sensitizers including, but not limited to, glitazone insulin sensitizers (such as thiazolidinediones), biguamides or a glucosidase inhibitors.

Additionally, the compounds of the present invention may further be administered in combination with a sulfamate compound of Formula (I) as disclosed in Maryanoff et al., U.S. Pat. No. 4,513,006, which is hereby incorporated by reference, in its entirety. A particularly preferred sulfamate compound disclosed in Maryanoff et al., in U.S. Pat. No. 4,513,006 is topiramate, also known by its chemical name 2,3:4,5-di-O-isopropylidene-(β)-D-fructopyranose sulfamate, a compound of the following structure:

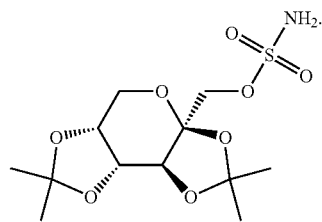

The sulfamate compounds of Formula (I) as disclosed in Maryanoff et al., U.S. Pat. No. 4,513,006 are useful in treating, preventing and/or preventing the progression of various disorders and diseases, including, but not limited to (a) epilepsy and related disorders; (b) diabetes, Syndrome X, impaired oral glucose tolerance and other metabolic disorders; (c) elevated blood pressure; (d) elevated lipid levels; (e) obesity and overweight condition, as would be recognized by one skilled in the art.

Preferably, one or more of the compounds of the present invention are administered in combination with topiramate for the treatment of a disorder selected from the group consisting of diabetes, inflammatory diseases, dermatological disorders, and CNS disorders. Preferably, the topiramate is administered in an amount in the range of from about 10 to about 400 mg per day, more preferably from about 25 to about 250 mg per day, more preferably from about 25 to about 200 mg per day.

The combination product is a product that comprises the co-administration of a compound of Formula (I) or a pharmaceutical composition thereof and an additional agent for treating or ameliorating a kinase mediated disorder, or for treating a disorder selected from the group consisting of diabetes, inflammatory diseases, dermatological disorders, and CNS disorders.

The term "combination product" further comprises a product that is sequentially administered where the product comprises a compound of Formula (I) or pharmaceutical composition thereof and an additional agent, administration of a pharmaceutical composition containing a compound of Formula (I) or pharmaceutical composition thereof and an additional agent or the essentially simultaneous administration of a separate pharmaceutical composition containing a compound of Formula (I) or pharmaceutical composition thereof and a separate pharmaceutical composition containing an additional agent.

The ubiquitous nature of the GSK isoforms and their important roles in physiology provide incentive to produce highly selective GSK inhibitors. Given the evidence demonstrating linkage of certain isoforms to disease states, it is reasonable to assume that inhibitory compounds that are selective to a GSK isoform relative to the other GSK isoforms and other protein kinases are superior therapeutic agents. Such compounds should demonstrate greater efficacy and lower toxicity by virtue of their specificity. Accordingly, it will be appreciated by one skilled in the art that a particular compound of Formula (I) is selected where it is therapeutically effective for a particular kinase mediated disorder based on the modulation of the disorder through the demonstration of selective kinase inhibition in response to that compound.

Experiments exemplifying selective kinase inhibition are provided in the examples. The usefulness of a compound of Formula (I) as a selective kinase inhibitor can be determined according to the methods disclosed herein and based on the data obtained to date, it is anticipated that a particular compound will be useful in inhibiting one or more kinase mediated disorders and therefore is useful in one or more kinase mediated disorders.

The term "selective kinase inhibitor" includes compounds of the present invention that exhibit high selectivity for a particular kinase, for example GSK-3 kinase, as compared to other kinases. Preferably, the compounds of the present invention possess high selectivity, defined herein as an approximate ten-fold selectivity, for GSK-3 kinase over other kinases, more preferably a fifty-fold selectivity, and most preferably one hundred-fold selectivity. One implication of this selectivity is that the compounds of the present invention display a reduced potential for side effects in a subject who has been administered such compounds.

Therefore, the term "kinase mediated disorders" as used herein, includes, and is not limited to, diabetes, inflammatory diseases, dermatological disorders, and CNS disorders.

Inflammatory diseases include, and are not limited to, vascular permeability, inflammation, asthma, rheumatoid arthritis or osteoarthritis.

Dermatological disorders include, and are not limited to, psoriasis, hair loss or baldness.

CNS disorders include, and are not limited to, chronic pain, neuropathic pain, epilepsy, chronic neurodegenerative conditions (such as dementia or Alzheimer's disease), mood disorders (such as schizophrenia), manic depression (also known as bipolar disorder) or neurotraumatic, cognitive decline and ischemia-related diseases (as a result of head trauma (from acute ischemic stroke, injury or surgery) or transient ischemic stroke (from coronary bypass surgery or other transient ischemic conditions)).

Another embodiment of the present invention is a method of treating a disorder selected from the group consisting of diabetes, inflammatory diseases, dermatological disorders, and CNS disorders comprising administering to a subject in need thereof a compound of Formula (I) or a pharmaceutical composition of the present invention.

General Synthetic Methods

Representative compounds of the present invention can be synthesized in accordance with the general synthetic methods described below and are illustrated in the schemes that follow. Since the schemes are an illustration, the invention should not be construed as being limited by the chemical reactions and conditions expressed. The preparation of the various starting materials used in the schemes is well within the skill of persons versed in the art.

Abbreviations used in the instant specification, particularly the Schemes and Examples, are as follows:

| Abbreviation | Meaning |
| --- | --- |
| Ar | aryl group |
| Cp | Cyclopentadienide |
| DMF | N,N-dimethylformamide |
| EDTA | ethylene diamine tetraacetic acid |
| EtOAc | ethyl acetate |
| MeOH | Methanol |
| MOPS | (3-(N-morpholino) propanesulfonic acid) |
| MTBE | methyl tert-butyl ether |
| NaH | Sodium hydride |
| PPh$_3$ | triphenylphosphine |
| RT or rt | room temperature |
| THF | Tetrahydrofuran |
| TLC | thin layer chromatography |

Scheme A describes the preparation of certain intermediates and compounds of the present invention.

Scheme A

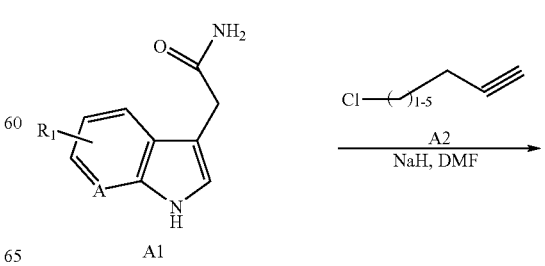

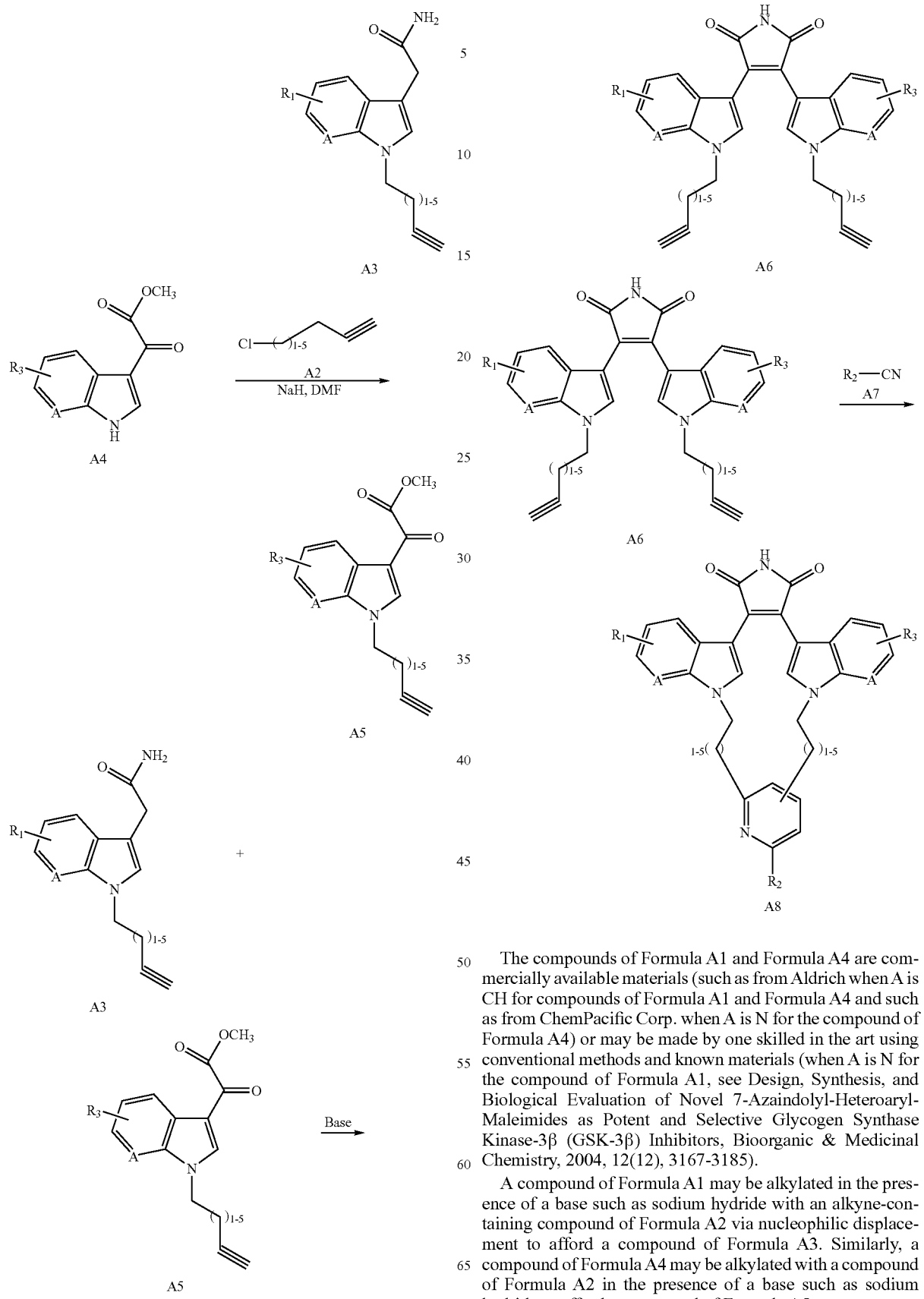

The compounds of Formula A1 and Formula A4 are commercially available materials (such as from Aldrich when A is CH for compounds of Formula A1 and Formula A4 and such as from ChemPacific Corp. when A is N for the compound of Formula A4) or may be made by one skilled in the art using conventional methods and known materials (when A is N for the compound of Formula A1, see Design, Synthesis, and Biological Evaluation of Novel 7-Azaindolyl-Heteroaryl-Maleimides as Potent and Selective Glycogen Synthase Kinase-3β (GSK-3β) Inhibitors, Bioorganic & Medicinal Chemistry, 2004, 12(12), 3167-3185).

A compound of Formula A1 may be alkylated in the presence of a base such as sodium hydride with an alkyne-containing compound of Formula A2 via nucleophilic displacement to afford a compound of Formula A3. Similarly, a compound of Formula A4 may be alkylated with a compound of Formula A2 in the presence of a base such as sodium hydride to afford a compound of Formula A5.

Condensation of a compound of Formula A3 with a compound of Formula A5 under basic conditions affords the alkyne-containing compound of Formula A6. Cobalt-mediated [2+2+2] co-cyclotrimerization of compound A6 with an $R_2$-substituted compound of Formula A7 in the presence of a cobalt catalyst such as $CpCo(CO)_2$ under diluted condition affords pyridine-containing macrocycle of Formula A8.

Accordingly, the present invention is directed to a process for synthesizing a compound of Formula (I):

Formula (I)

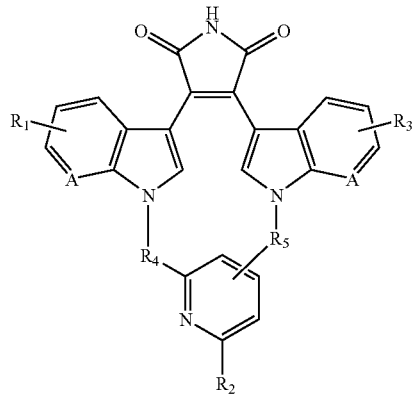

wherein
A is CH or N, to form 1H-indole or 1H-pyrrolo[2,3-b]pyridine, respectively;
$R_1$ and $R_3$ are each selected from the group consisting of hydrogen, $C_{1-4}$alkyl, $C_{2-4}$alkenyl, $C_{1-4}$alkoxy, $C_{1-4}$alkylthio, halogen, trifluoromethyl, trifluoromethoxy, hydroxy, hydroxy($C_{1-4}$)alkyl, nitro, amino, ($C_{1-4}$)alkylamino, and di($C_{1-4}$)alkylamino;
$R_4$ and $R_5$ are each $C_{2-6}$alkylene optionally substituted with oxo, wherein the point of attachment for $R_5$ is meta or ortho relative to the $R_2$ substituted pyridine carbon ring atom of the compound of Formula (I);
$R_2$ is $C_{6-10}$aryl or $NR_aR_b$; wherein $C_{6-10}$aryl is optionally substituted with one, two or three substituents independently selected from the group consisting of $C_{1-4}$alkyl, $C_{1-4}$alkoxy, halogen, amino, ($C_{1-4}$)alkylamino, di($C_{1-4}$)alkylamino, and $C_{1-4}$alkoxycarbonyl;
$R_a$ and $R_b$ are each $C_{1-6}$alkyl; or, $R_a$ and $R_b$ are taken together with the atoms to which they are attached to form a 5, 6, 7 or 8 membered monocyclic ring; wherein said monocyclic ring optionally contains one additional oxygen, sulfur, NH, or N($C_{1-4}$alkyl);

comprising the steps of:
Step A. reacting a compound of Formula A1 in the presence of a base with a compound of Formula A2 to provide a compound of Formula A3:

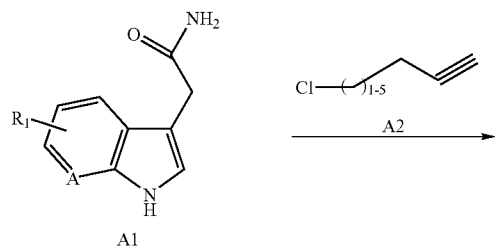

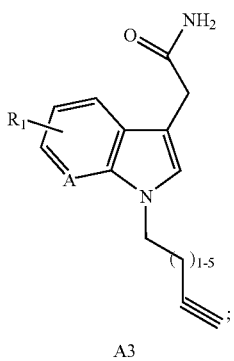

Step B. reacting a compound of Formula A4 in the presence of a base with the compound of Formula A2 to provide a compound of Formula A5:

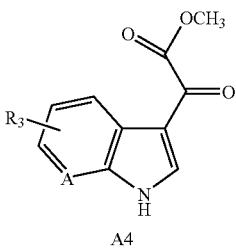 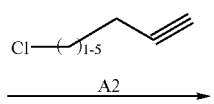

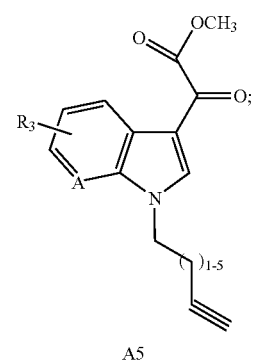

Step C. reacting the compound of Formula A3 in the presence of a base with the compound of Formula A5 to provide a compound of Formula A6:

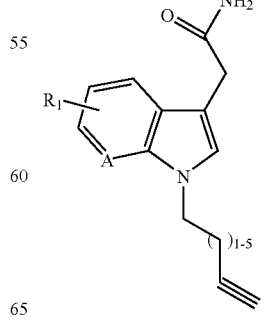 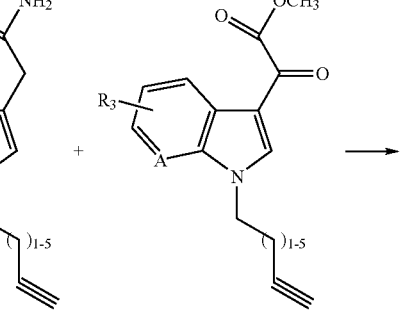

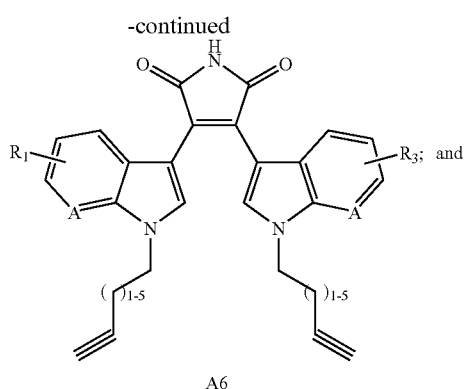

Step D. reacting the compound of Formula A6 with the compound of Formula A7 in the presence of a cobalt catalyst to provide a compound of Formula A8, representative of a compound of Formula (I):

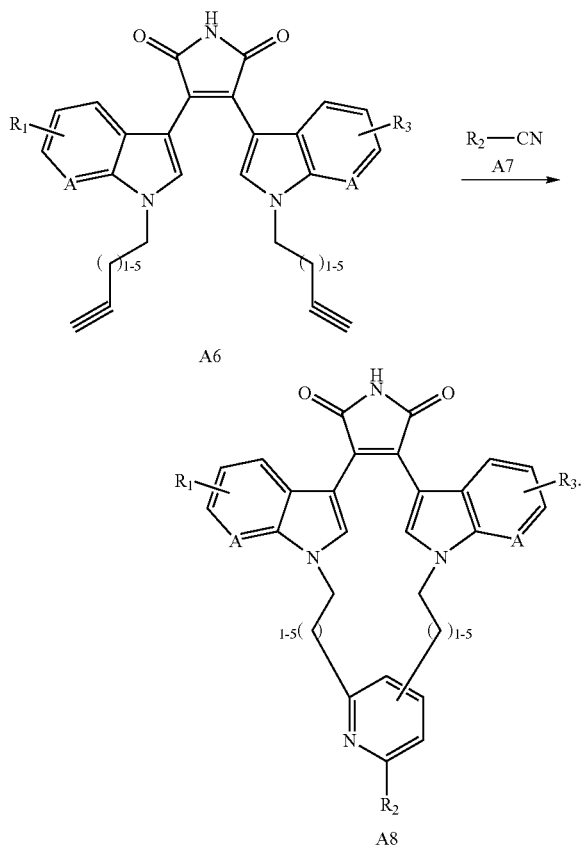

In Steps A and B, a typical base is sodium hydride and the like in a solvent such as DMF and the like.

In Step D, the compound of Formula A6 is present in a range of from about 1 molar equivalent to about 10 molar equivalents; or, in a range of from about 4 molar equivalents to about 8 molar equivalents.

In Step D, a typical cobalt catalyst is CpCo(CO)$_2$ in an aprotic organic solvent (selected from toluene, 1,4-dioxane, dimethoxyethane and the like, preferably, 1,4-dioxane or dimethoxyethane).

In Step D, the cobalt catalyst is present in a range of from about 0.1 molar equivalents to about 1 molar equivalent; or, in a range of from about 0.2 molar equivalents to about 0.5 molar equivalents.

In an example of the process, the reaction of the compound of Formula A6 with the compound of Formula A7 is optionally conducted in the presence of triphenylphosphine, is optionally at an elevated temperature and is optionally under an inert atmosphere.

In an example of the process, the temperature is in a range of from about 60° C. to about 140° C.; or, in a range of from about 80° C. to about 110° C.

In an example of the process, triphenylphosphine is present in a range of from about 0.1 molar equivalents to about 1 molar equivalent; or, in a range of from about 0.2 molar equivalents to about 0.5 molar equivalents.

In an example of the process, the inert atmosphere is Argon.

In an example of the process, the compound of Formula (I) is selected from a compound wherein:

A is CH such that the A-containing ring system of Formula (I) is 1H-indole;

$R_1$ and $R_3$ are each selected from the group consisting of hydrogen, methyl, methoxy, halogen, and hydroxy;

$R_4$ and $R_5$ are each $C_{3-4}$alkylene;

$R_2$ is $C_{6-10}$aryl or $NR_aR_b$; wherein $C_{6-10}$aryl is optionally substituted with one or two substituents independently selected from the group consisting of $C_{1-4}$alkyl and halogen; and $R_a$ and $R_b$ are each $C_{1-4}$alkyl; or $R_a$ and $R_b$ are taken together with the atoms to which they are attached to form a 5 to 6 membered monocyclic ring.

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

EXAMPLE 1

20-(dimethylamino)-4,14,19,26-tetraazaheptacyclo[24.6.1.1$^{7,14}$.1$^{18,22}$.0$^{2,6}$.0$^{8,13}$.0$^{27,32}$]pentatriaconta-1(33),2(6),7(35),8,10,12,18(34),19,21,27,29,31-dodecaene-3,5-dione (Cpd 2)

31-(dimethylamino)-5,15,25,30-tetraazaheptacyclo[27.2.2.1$^{5,12}$.1$^{18,25}$.0$^{6,11}$.0$^{13,17}$.0$^{19,24}$]pentatriaconta-1(31),6,8,10,12(35),13(17),18(34),19,21,23,29,32-dodecaene-14,16-dione (Cpd 3)

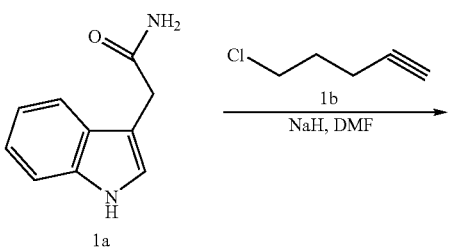

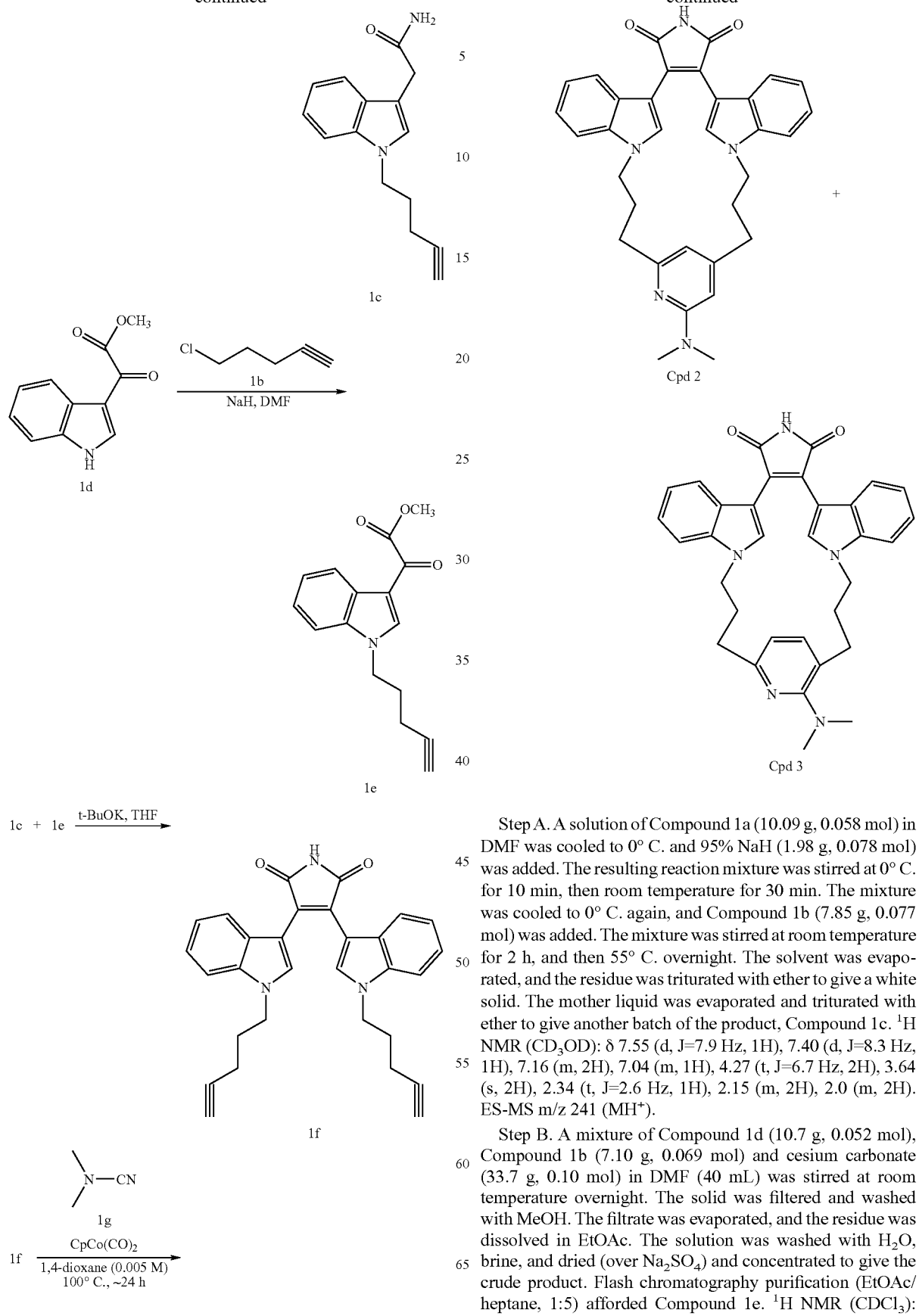

Step A. A solution of Compound 1a (10.09 g, 0.058 mol) in DMF was cooled to 0° C. and 95% NaH (1.98 g, 0.078 mol) was added. The resulting reaction mixture was stirred at 0° C. for 10 min, then room temperature for 30 min. The mixture was cooled to 0° C. again, and Compound 1b (7.85 g, 0.077 mol) was added. The mixture was stirred at room temperature for 2 h, and then 55° C. overnight. The solvent was evaporated, and the residue was triturated with ether to give a white solid. The mother liquid was evaporated and triturated with ether to give another batch of the product, Compound 1c. $^1$H NMR (CD$_3$OD): δ 7.55 (d, J=7.9 Hz, 1H), 7.40 (d, J=8.3 Hz, 1H), 7.16 (m, 2H), 7.04 (m, 1H), 4.27 (t, J=6.7 Hz, 2H), 3.64 (s, 2H), 2.34 (t, J=2.6 Hz, 1H), 2.15 (m, 2H), 2.0 (m, 2H). ES-MS m/z 241 (MH$^+$).

Step B. A mixture of Compound 1d (10.7 g, 0.052 mol), Compound 1b (7.10 g, 0.069 mol) and cesium carbonate (33.7 g, 0.10 mol) in DMF (40 mL) was stirred at room temperature overnight. The solid was filtered and washed with MeOH. The filtrate was evaporated, and the residue was dissolved in EtOAc. The solution was washed with H$_2$O, brine, and dried (over Na$_2$SO$_4$) and concentrated to give the crude product. Flash chromatography purification (EtOAc/heptane, 1:5) afforded Compound 1e. $^1$H NMR (CDCl$_3$):

δ 8.46 (m, 2H), 7.43 (m, 1H), 7.35 (m, 2H), 4.37 (t, J=6.7 Hz, 2H), 3.96 (s, 3H), 2.22 (m, 2H), 2.11 (m, 3H). ES-MS m/z 270 (MH+).

Step C. A solution of 1.0 M potassium t-butoxide in THF (23 mL, 23 mmol) was added dropwise to a suspension of the ester Compound 1e (2.47 g, 9.17 mmol) and the amide Compound 1c (1.84 g, 7.64 mmol) in dry THF (18 mL) under Argon that had been cooled to 0° C. The resulting mixture was stirred at 0° C. for 5 min and room temperature for 20 min, to which was then added ice water and EtOAc. The organic layer was separated and the aqueous layer was extracted with EtOAc (4×). The combined extracts were sequentially washed with water, saturated aq. $NaHCO_3$, brine and then dried ($Na_2SO_4$) and evaporated in vacuo. The crude product was purified by flash chromatography (EtOAc/Hexane, 1:3) to give Compound 1f as an orange solid. $^1$H NMR (CDCl$_3$): δ 7.67 (s, 2H), 7.32 (m, 3H), 7.12 (m, 2H), 7.05 (m, 2H), 6.75 (m, 2H), 4.30 (t, J=6.7 Hz, 4H), 2.17 (m, 4H), 2.06 (m, 6H). ES-MS m/z 460 (MH+).

Step D. Typical Procedure for Cobalt-Mediated [2+2+2] Co-Cyclotrimerization: Synthesis of Pyridine-Containing Macrocycles. In a 100-mL round-bottom flask, equipped with a condenser and a three-way stopper connected to a balloon of argon, a mixture of Compound 1f (86 mg, 0.19 mmol) and dimethyl cyanamide (66 mg, 0.94 mmol, 5 mol equiv) was pumped briefly and purged twice with argon. 15 mL of 1,4-dioxane was then added, followed by a 10-mL dioxane solution of CpCo(CO)$_2$ (8.2 μL, 0.065 mmol, 34 mol %), and the remaining volume of the solvent to provide a final 0.005 M concentration (relative to Compound 1f). The resulting solution was then heated at reflux for 22 h. The reaction was checked by TLC, and the mixture was added with additional CpCo(CO)$_2$ (4.0 μL; total amount; 12.2 μL, 0.097 mmol, 51 mol %). The reaction mixture was stirred for an additional two hours at reflux, and was then cooled to room temperature. Subsequent removal of the solvents in vacuo, followed by flash chromatography (silica gel, EtOAc/hexanes, 1:10, 1:4, 1:2 and then 1:1) afforded Compound 2 and Compound 3. (Note: For best results, newly opened bottles of anhydrous 1,4-dioxane (Sigma-Aldrich) and CpCo(CO)$_2$ (Strem Chemicals) should be used in these reactions.)

Compound 2 (meta isomer): $^1$H NMR (CDCl$_3$, 600 MHz): δ 7.75 (d, J=8.0 Hz, 1H), 7.47 (s, 2H), 7.35 (d, J=7.7 Hz, 1H), 7.33 (d, J=7.9 Hz, 1H), 7.32 (d, J=8.1 Hz, 1H), 7.25 (t, J=7.9 Hz, 1H), 7.19 (t, J=7.9 Hz, 1H), 7.16 (t, J=8.0 Hz, 1H), 7.15 (s, 1H), 7.02 (d, J=7.7 Hz, 1H), 6.04 (s, 1H), 4.57 (s, 1H), 4.17 (t, J=5.6 Hz, 2H), 3.95 (t, J=5.4 Hz, 2H), 3.03 (s, 6H), 2.36 (t, J=6.4 Hz, 2H), 2.10-2.19 (m, 6H). $^{13}$C NMR (CDCl$_3$, 150 MHz): δ 171.7, 171.6, 159.5, 158.5, 151.9, 136.7, 136.5, 132.9, 132.5, 130.1, 129.0, 125.8, 125.4, 122.6, 122.5, 122.4, 120.9, 120.8, 111.6, 110.6, 110.1, 105.0, 104.7, 102.5, 46.8, 45.4, 38.0, 32.9, 32.0, 31.3, 28.8, 27.0. HRMS (FAB): Calcd for $C_{33}H_{31}N_5O_2^+$: 529.2478; Found: 529.2475.

Compound 3 (para isomer): $^1$H NMR (CDCl$_3$, 600 MHz): δ 7.46 (d, J=8.2 Hz, 1H), 7.36 (d, J=8.7 Hz, 1H), 7.33 (s, 1H), 7.25 (d, J=8.1 Hz, 1H), 7.23 (d, J=8.5 Hz, 1H), 7.19 (t, J=7.7 Hz, 1H), 7.17 (t, J=7.6 Hz, 1H), 7.03 (d, J=7.4 Hz, 1H), 7.00 (t, J=7.7 Hz, 1H), 6.96 (t, J=7.4 Hz, 1H), 6.67 (s, 1H), 6.31 (d, J=7.6 Hz, 1H), 4.18 (t, J=5.5 Hz, 2H), 3.91 (broad s, 2H), 2.68 (broad s, 6H), 2.63 (s, 6H), 2.31 (broad s, 2H). $^{13}$C NMR (CDCl$_3$, 150 MHz): δ 172.0, 161.2, 154.9, 137.1, 136.6, 136.3, 134.0, 133.4, 127.8, 127.3, 124.6, 124.3, 123.3, 123.1, 122.0, 121.9, 121.7, 120.3, 120.0, 115.5, 109.6, 109.5, 104.8, 104.7, 46.3, 45.1, 41.6, 34.2, 28.0, 25.6, 25.3. HRMS (FAB): Calcd for $C_{33}H_{31}N_5O_2^+$: 529.2478; Found: 529.2457.

EXAMPLE 2

20-pyrrolidin-1-yl-4,14,19,26-tetraazaheptacyclo [24.6.1.1$^{7,14}$.1$^{18,22}$.0$^{2,6}$.0$^{8,13}$.0$^{27,32}$]pentatriaconta-1 (33),2(6),7(35),8,10,12,18(34),19,21,27,29,31-dodecaene-3,5-dione (Cpd 6)

31-pyrrolidin-1-yl-5,15,25,30-tetraazaheptacyclo [27.2.2.1$^{5,12}$.1$^{18,25}$.0$^{6,11}$.0$^{13,17}$.0$^{19,24}$]pentatriaconta-1(31),6,8,10,12(35),13(17),18(34),19,21,23,29,32-dodecaene-14,16-dione (Cpd 7)

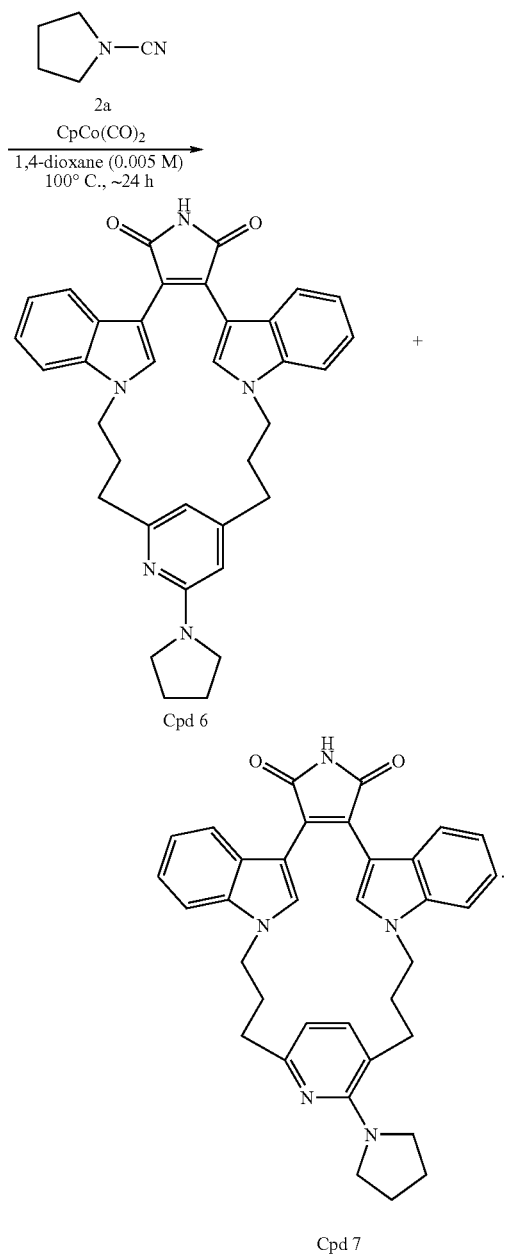

Cpd 6

Cpd 7

Compounds 6 and 7 were prepared according to Example 1, substituting 1H-pyrrolidine cyanamide for dimethyl cyanamide in Step D. In a 100-mL round-bottom flask, equipped with a condenser and a three-way stopper connected to a balloon of argon, a mixture of Compound 1f (75 mg, 0.16 mmol) and pyrrolidine cyanamide (78 mg, 0.81 mmol) was pumped briefly and purged twice with argon. 15 mL of 1,4-dioxane was then added, followed by a 10-mL dioxane solution of $CpCo(CO)_2$ (7.2 μL, 0.057 mmol, 36 mol %), and the remaining volume of the solvent to provide a final 0.005 M concentration (relative to Compound 1f). The resulting solution was then heated at reflux for 22 h. The reaction was checked by TLC, and the mixture was added with additional $CpCo(CO)_2$ (4.0 μL; total amount: 12.2 μL, 0.097 mmol, 51 mol %). The reaction mixture was stirred for an additional two hours at reflux, and was then cooled to room temperature. Subsequent removal of the solvents in vacuo, followed by flash chromatography (silica gel, EtOAc/hexanes, 1:10, 1:4, 1:2 and then 1:1) afforded Compound 6 and Compound 7.

Compound 6: $^1H$ NMR ($CDCl_3$, 500 MHz): δ 7.63 (m, 1H), 7.35 (m, 2H), 7.21 (m, 3H), 7.11 (m, 1H), 7.08 (m, 1H), 7.02 (m, 1H), 6.92 (m, 1H), 5.78 (m, 1H), 4.47 (m, 1H), 4.05 (m, 2H), 3.87 (m, 2H), 3.25 (m, 6H), 2.22 (m, 2H), 2.04 (m, 4H), 1.93 (m, 4H). ES-MS m/z 556 ($MH^+$).

Compound 7: $^1H$ NMR ($CDCl_3$, 300 MHz): δ 7.82 (s, 1H), 7.55 (d, J=7.9 Hz, 1H), 7.34 (d, J=8.2 Hz, 1H), 7.22 (m, 2H), 7.03 (m, 5H), 6.81 (m, 1H), 6.03 (d, J=7.4 Hz, 1H), 4.14 (t, J=5.6 Hz, 2H), 3.92 (m, 2H), 3.27 (m, 4H), 2.72 (m, 2H), 2.32 (m, 6H), 1.83 (m, 4H). ES-MS m/z 556 ($MH^+$).

EXAMPLE 3

31-(dimethylamino)-5,15,25,32-tetraazaheptacyclo [28.2.2.1$^{5,12}$.1$^{18,25}$.0$^{6,11}$.0$^{3,17}$.0$^{9,24}$]hexatriaconta-1 (32),6,8,10,12(36),13(17),18(35),19,21,23,30,33-dodecaene-14,16-dione (Cpd 1)

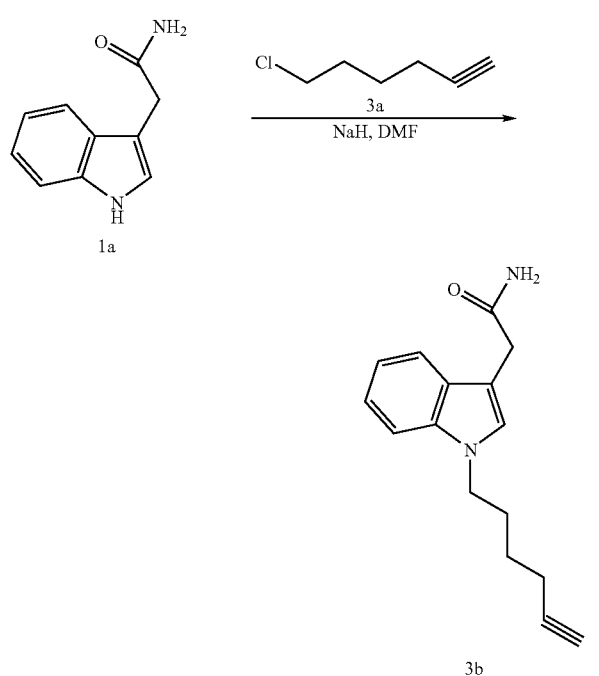

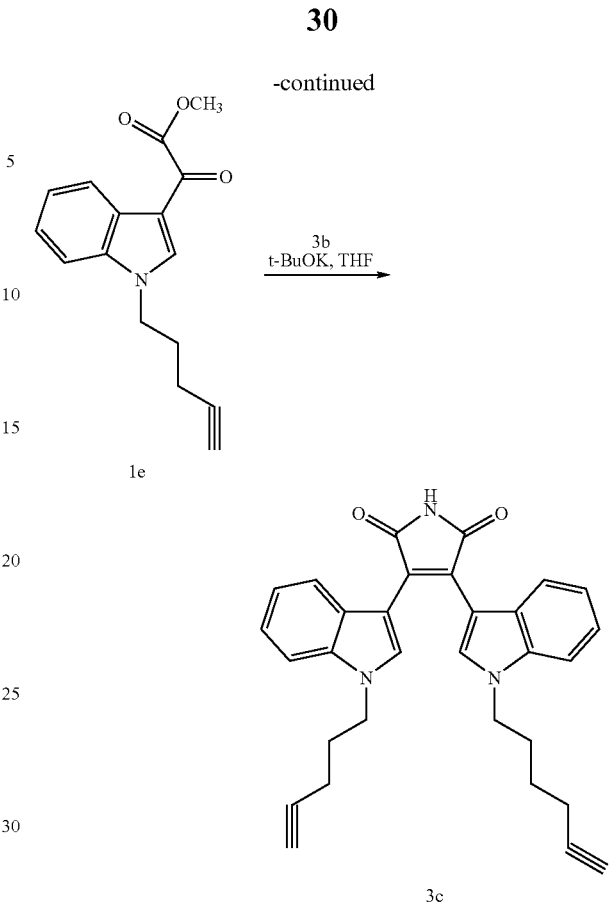

Step A. A solution of Compound 1a (2.06 g, 0.0118 mol) in DMF was cooled to 0° C. and 95% NaH (0.617 g, 0.0154 mol) was added. The resulting reaction mixture was stirred at 0° C. for 10 min, then room temperature for 30 min. The mixture was cooled to 0° C. again, and Compound 3a (2.01 g, 0.017 mol) was added. The mixture was stirred at room temperature for 2 h, and then 55° C. overnight. The solvent was evaporated, and the residue was triturated with ether to give a white solid. The mother liquid was evaporated and triturated with ether to give another batch of the product, affording Compound 3b. ¹H NMR (CDCl₃, 300 MHz): δ 7.55 (d, J=7.9 Hz, 1H), 7.36 (d, J=8.2 Hz, 1H), 7.16 (m, 2H), 7.04 (t, J=7.5 Hz, 1H), 4.16 (m, 2H), 3.64 (s, 2H), 2.19 (m, 3H), 1.95 (m, 2H), 1.49 (m, 2H). ES-MS m/z 255 (MH⁺).

Step B. A solution of 1.0 M potassium t-butoxide in THF (2.0 mL, 2 mmol) was added dropwise to a suspension of the ester Compound 1e (0.388 g, 1.44 mmol) and the amide Compound 3b (0.3 g, 1.18 mmol) in dry THF (2 mL) under Argon that had been cooled to 0° C. The resulting mixture was stirred at 0° C. for 15 min and room temperature for 2 h, to which was then quenched with H₂O (10 mL), added EtOAc (15 mL), extracted with EtOAc (5×15 mL). The combined extracts were sequentially washed with 1N HCl (5 mL) and then H₂O (3×20 mL), brine (2×20 mL) and then dried (MgSO₄) and evaporated in vacuo. The crude product was purified by flash chromatography (EtOAc/Hexane, 1:2) to give Compound 3c as an orange solid. ¹H NMR (CDCl₃, 500 MHz): δ 8.08 (bs, 1H), 7.68 (d, J=3.9 Hz, 2H), 7.30 (dd, J=6.0, 8.3 Hz, 2H), 7.7 (t, J=8.2 Hz, 2H), 6.95 (dd, J=7.9, 8.0 Hz, 2H), 6.74 (m, 2H), 4.28 (t, J=6.7 Hz, 2H), 4.16 (t, J=7.0 Hz, 2H), 2.16 (m, 4H), 2.01 (m, 6H), 1.52 (m, 2H). ¹³C NMR (CDCl₃, 500 MHz): δ 172.8, 136.6, 136.5, 132.2, 132.1, 128.4, 128.1, 126.7, 122.7, 122.6, 120.6, 120.5, 110.0, 106.4, 106.2, 84.0, 83.1, 70.3, 69.6, 46.7, 45.5, 29.4, 29.0, 26.0, 18.5, 16.2. ES-MS m/z 474 (MH⁺).

Step C. Compound 1 was prepared according to the methods described in Example 1, Step D, substituting Compound 3c for Compound 1f. Compound 1: ¹H NMR (CDCl₃, 500 MHz): δ 7.37 (m, 2H), 7.28 (d, J=8.3 Hz, 1H), 7.21 (dd, J=1.0, 7.1 Hz, 1H), 7.18 (m, 1H), 7.03 (m, 2H), 6.95 (d, J=7.5 Hz, 2H), 6.78 (t, J=7.2 Hz, 1H), 6.45 (d, J=7.4 Hz, 1H), 4.07 (t, J=6.0 Hz, 4H), 2.73 (m, 2H), 2.66 (s, 6H), 2.51 (t, J=6.9 Hz, 2H), 2.42 (m, 2H), 1.51 (t, J=6.1 Hz, 2H), 1.25 (m, 2H). ¹³C NMR (CDCl₃, 500 MHz): δ 171.9, 171.8, 161.1, 155.1, 138.24, 136.6, 136.5, 133.6, 131.5, 130.1, 127.0, 125.6, 124.8, 124.7, 122.7, 122.3, 122.2, 121.8, 120.35, 120.3, 116.5, 109.9, 109.6, 105.3, 105.0, 46.5, 44.7, 42.5, 34.7, 29.0, 28.1, 27.4, 26.4. ES-MS m/z 544 (MH⁺).

EXAMPLE 4

33-pyrrolidin-1-yl-6,16,26,32-tetraazaheptacyclo[29.2.2.1⁶,¹³.1¹⁹,²⁶.0⁷,¹².0¹⁴,¹⁸.0²⁰,²⁵]heptatriaconta-1(33),7,9,11,13(37),14(18),19(36),20,22,24,31,34-dodecaene-15,17-dione (Cpd 5)

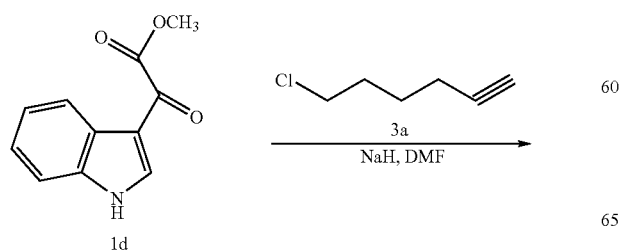

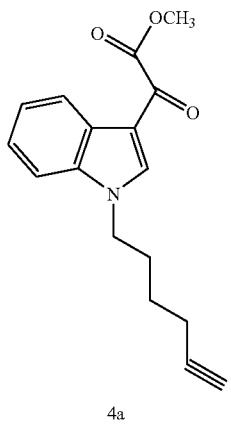

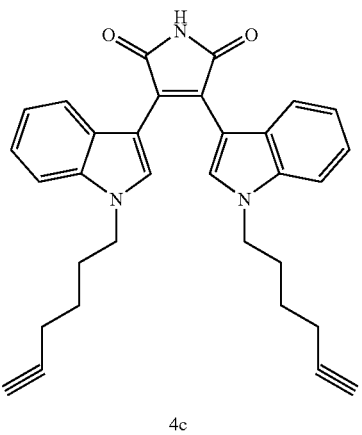

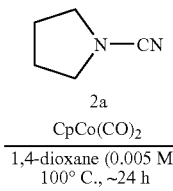

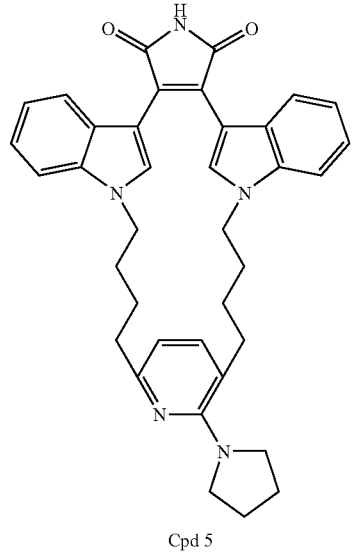

Step A. Compound 4a was prepared according to the methods described in Example 1, Step A, substituting Compound 3a for Compound 1b. ES-MS m/z 284 (MH+).

Step B. A solution of 1.0 M potassium t-butoxide in THF (9.6 mL, 9.6 mmol) was added dropwise to a suspension of the ester Compound 4a (1.22 g, 4.30 mmol) and the amide Compound 3b (0.812 g, 3.19 mmol) in dry THF (6.5 mL) under Argon that had been cooled to 0° C. The resulting mixture was stirred at 0° C. for 5 min and room temperature for 20 min, to which was then added ice water and EtOAc. The organic layer was separated and the aqueous layer was extracted with EtOAc (4×). The combined extracts were sequentially washed with water, saturated aq. $NaHCO_3$, brine and then dried ($Na_2SO_4$) and evaporated in vacuo. The crude product was purified by flash chromatography (EtOAc/Hexane, 1:3) to give Compound 4c as an orange solid. $^1$H NMR (CDCl$_3$, 300 MHz): δ 7.60 (m, 2H), 7.28 (m, 2H), 7.08 (t, J=8.0 Hz, 2H), 6.95 (d, J=8.0 Hz, 2H), 6.74 (m, 2H), 4.18 (t, J=7.0 Hz, 4H), 2.22 (m, 4H), 1.97 (m, 6H), 1.53 (m, 4H). ES-MS m/z 488 (MH+).

Step C. Compound 5 was prepared according to the methods described in Example 1, Step D, substituting Compound 4c for Compound 1f, and substituting pyrrolidine cyanamide for Compound 1g. Compound 5: $^1$H NMR (CDCl$_3$, 300 MHz): δ 7.35 (m, 2H), 7.29 (m, 1H), 7.19 (m, 5H), 7.00 (m, 3H), 6.28 (d, J=7.2 Hz, 1H), 3.90 (m, 4H), 3.30 (m, 4H), 2.61 (m, 4H), 1.82 (m, 4H), 1.48 (m, 8H). ES-MS m/z 584 (MH+).

EXAMPLE 5

20-(4-methylphenyl)-4,14,19,26-tetraazaheptacyclo[24.6.1.1$^{7,14}$.1$^{18,22}$.0$^{2,6}$.0$^{8,13}$.0$^{27,32}$]pentatriaconta-1(33),2(6),7(35),8,10,12,18(34),19,21,27,29,31-dodecaene-3,5-dione (Cpd 4)

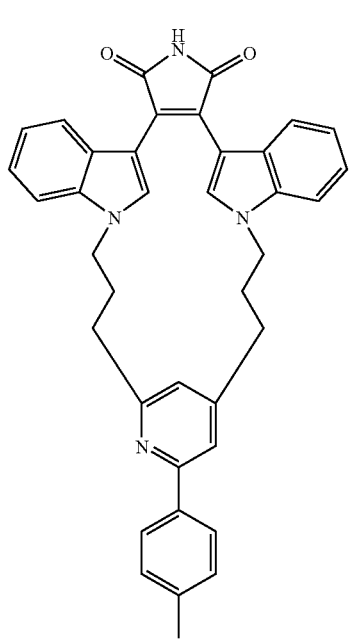

Cpd 4

Compound 4 was prepared according to the procedure described in Example 1, substituting p-tolunitrile for Compound 1g in Step D. Compound 4: $^1$H NMR (CDCl$_3$, 300 MHz): δ 7.80 (d, J=8.0 Hz, 2H), 7.62 (d, J=7.5 Hz, 1H), 7.41 (d, J=8.0 Hz, 2H), 7.38 (s, 1H), 7.31 (m, 3H), 7.20 (m, 5H), 7.08 (m, 2H), 4.13 (m, 2H), 4.05 (m, 2H), 2.42 (m, 2H), 2.39 (m, 3H), 2.35 (m, 4H), 2.19 (m, 2H). ES-MS m/z 577 (MH+).

EXAMPLE 6

Alternative Procedure for Cobalt-Mediated [2+2+2] Co-Cyclotrimerization

In a 100-mL round-bottom flask, equipped with a condenser and a three-way stopper connected to a balloon of argon, a mixture of Compound 1f (60 mg, 0.13 mmol), PPh$_3$ (17 mg, 0.065 mmol) and dimethyl cyanamide (45.8 mg, 0.65 mmol, 5 mol equiv) was pumped briefly and purged twice with argon. 10 mL of 1,4-dioxane was then added, followed by a 10-mL dioxane solution of CpCo(CO)$_2$ (12 µL, 0.065 mmol, 34 mol %), and the remaining volume of the solvent to provide a final 0.005 M concentration (relative to Compound 1f). The resulting solution was then heated at 110° C. for 36 h. The volatiles were removed under vacuo and the crude product was separated by flash chromatography (silica gel, CH$_2$Cl$_2$/MeOH/NH$_4$OH, 97:3:0.3) to afford Compound 2 and Compound 3.

The procedure described in Example 6 demonstrated a significant improvement of yield of cyclotrimerization over the procedure described in Step D of Example 1 (69% vs. 21%).

EXAMPLE 7

As a specific embodiment of an oral composition, 100 mg of Compound 1 is formulated with a sufficiently finely divided lactose to provide a total amount of 580 to 590 mg to fill a size 0 hard gel capsule.

BIOLOGICAL EXAMPLES

Example 1

Glycogen Synthase Kinase-3 Assay

Compounds were tested for the ability to inhibit GSK-3β protein. Briefly, in a final reaction volume of 25 µL, GSK-3β (h) (5-10 mU) was incubated with 8 mM MOPS pH 7.0, 0.2 mM EDTA, 20 µM YRRAAVPPSPSLSRHSSPHQS(p)EDEEE (phospho GS2 peptide), 10 mM Mg Acetate and [γ-$^{33}$P-ATP] (specific activity approx. 500 cpm/pmol, concentration as required). The reaction was initiated by the addition of the MgATP mix. After incubation for 40 minutes at room temperature, the reaction was stopped by the addition of 5 µL of a 3% phosphoric acid solution. 10 µL of the reaction was then spotted onto a P30 filtermat and washed three times for 5 minutes in 50 mM phosphoric acid and once in methanol prior to drying and scintillation counting.

Table 1 shows the biological activity in the GSK-3β assay as IC$_{50}$ values (µM) for representative compounds of the present invention. The GSK-3β assay was run three times for each compound.

TABLE 1

| GSK-3β Assay Activity (IC$_{50}$ µM) | |
|---|---|
| Cpd | GSK-3β |
| 1 | 0.0006, 0.0015, 0.0081 |
| 2 | 0.0014, 0.0082, 0.0123 |
| 3 | 0.0055, 0.0529, 0.0521 |
| 4 | 0.010, 0.021, 0.0535 |

TABLE 1-continued

GSK-3β Assay Activity (IC$_{50}$ μM)

| Cpd | GSK-3β |
|---|---|
| 5 | 0.024, 0.0193, 0.0298 |
| 6 | 0.027, 0.0029, 0.0038 |
| 7 | 0.058, 0.0129, 0.0193 |

Example 2

Protein Kinase Selectivity Assays Using a Protein Kinase Selectivity Panel

Protein kinase selectivity assays were performed as described in the scientific literature (Davies, S. P., et al., Biochem. J. 2000, 351, 95-105). Briefly, protein kinases were assayed for their ability to phosphorylate the appropriate peptide/protein substrates in the presence of 1.0 μM compound. Assays were done using 10 μM ATP and were linear with respect to time. The protein kinase selectivity assays were performed by Upstate Cell Signaling Solutions using Upstate's KinaseProfiler™ Selectivity Screening Service. A copy of the Upstate KinaseProfiler™ Selectivity Screening Service Assay Protocols is attached hereto as Exhibit A.

Table 2 shows the screening results of Compounds 1, 2, 6 and 7 against 101 protein kinases in the Upstate panel.

TABLE 2

Activity at Protein Kinase Assays (% of control)

| Protein Kinase | Cpd 1 | Cpd 2 | Cpd 6 | Cpd 7 |
|---|---|---|---|---|
| Abl(h) | 105 | 98 | 107 | 108 |
| Abl(m) | 98 | 108 | 104 | 110 |
| Abl(T315I)(h) | 100 | 79 | 77 | 103 |
| ALK(h) | 103 | 55 | 58 | 74 |
| AMPK(r) | 101 | 101 | 105 | 99 |
| Arg(m) | 113 | 129 | 121 | 130 |
| Aurora-A(h) | 109 | 111 | 111 | 106 |
| Axl(h) | 97 | 104 | 106 | 100 |
| Blk(m) | 109 | 70 | 74 | 91 |
| Bmx(h) | 101 | 159 | 173 | 176 |
| BTK(h) | 105 | 106 | 106 | 104 |
| c-RAF(h) | 103 | 87 | 92 | 85 |
| CaMKII(r) | 92 | 107 | 109 | 98 |
| CaMKIV(h) | 92 | 113 | 112 | 99 |
| CDK1/cyclinB(h) | 78 | 98 | 80 | 98 |
| CDK2/cyclinA(h) | 120 | 80 | 88 | 88 |
| CDK2/cyclinE(h) | 54 | 84 | 88 | 88 |
| CDK3/cyclinE(h) | 59 | 89 | 86 | 106 |
| CDK5/p35(h) | 99 | 105 | 99 | 104 |
| CDK6/cyclinD3(h) | 86 | 74 | 82 | 92 |
| CDK7/cyclinH/MAT1(h) | 89 | 108 | 107 | 111 |
| CHK1(h) | 105 | 101 | 110 | 106 |
| CHK2(h) | 91 | 94 | 84 | 91 |
| CK1δ(h) | 107 | 111 | 112 | 109 |
| CK1(y) | 91 | 98 | 99 | 98 |
| CK2(h) | 107 | 111 | 108 | 113 |
| CSK(h) | 95 | 133 | 125 | 129 |
| cSRC(h) | 81 | 105 | 97 | 113 |
| EGFR(h) | 94 | 96 | 108 | 104 |
| EphB2(h) | 125 | 114 | 110 | 114 |
| EphB4(h) | 89 | 103 | 109 | 100 |
| Fes(h) | 107 | 133 | 139 | 130 |
| FGFR3(h) | 75 | 84 | 114 | 117 |
| Flt3(h) | 86 | 71 | 77 | 85 |
| Fms(h) | 94 | 101 | 99 | 106 |
| Fyn(h) | 103 | 106 | 106 | 103 |
| GSK3α(h) | 4 | 3 | 4 | 9 |
| GSK3β(h) | 1 | 1 | 3 | 7 |
| IGF-1R(h) | 84 | 37 | 42 | 106 |
| IKKα(h) | 92 | 133 | 132 | 121 |
| IKKβ(h) | 128 | 124 | 125 | 130 |
| IR(h) | 91 | 102 | 110 | 87 |
| JNK1α1(h) | 102 | 105 | 108 | 104 |
| JNK2α2(h) | 96 | 106 | 114 | 110 |
| JNK3(h) | 96 | 107 | 103 | 102 |
| Lck(h) | 96 | 100 | 99 | 90 |
| Lyn(h) | 107 | 76 | 87 | 78 |
| Lyn(m) | 90 | 102 | 99 | 104 |
| MAPK1(h) | 97 | 86 | 99 | 110 |
| MAPK2(h) | 102 | 104 | 92 | 88 |
| MAPK2(m) | 95 | 95 | 103 | 99 |
| MAPKAP-K2(h) | 98 | 101 | 108 | 95 |
| MEK1(h) | 76 | 93 | 91 | 98 |
| Met(h) | 121 | 132 | 129 | 132 |
| MKK4(m) | 130 | 119 | 119 | 113 |
| MKK6(h) | 102 | 86 | 91 | 85 |
| MKK7β(h) | 88 | 78 | 97 | 85 |
| MSK1(h) | 36 | 58 | 38 | 104 |
| MST2(h) | 103 | 84 | 100 | 86 |
| NEK2(h) | 104 | 102 | 105 | 99 |
| p70S6K(h) | 98 | 91 | 95 | 84 |
| PAK2(h) | 93 | 103 | 100 | 102 |
| PAR-1Bα(h) | 94 | 100 | 96 | 101 |
| PDGFRα(h) | 107 | 119 | 126 | 113 |
| PDGFRβ(h) | 147 | 101 | 103 | 105 |
| PDK1(h) | 115 | 104 | 107 | 100 |
| PKA(b) | 99 | 107 | 89 | 105 |
| PKA(h) | 90 | 95 | 104 | 102 |
| PKBα(h) | 94 | 114 | 112 | 106 |
| PKBβ(h) | 86 | 118 | 104 | 102 |
| PKBγ(h) | 93 | 106 | 103 | 105 |
| PKCα(h) | 68 | 74 | 82 | 83 |
| PKCβII(h) | 64 | 68 | 74 | 77 |
| PKCγ(h) | 91 | 107 | 99 | 102 |
| PKCδ(h) | 73 | 100 | 104 | 91 |
| PKCε(h) | 72 | 83 | 93 | 97 |
| PKCη(h) | 85 | 109 | 102 | 97 |
| PKCι(h) | 104 | 117 | 121 | 90 |
| PKCθ(h) | 21 | 27 | 29 | 33 |
| PKCμ(h) | 110 | 118 | 118 | 113 |
| PKCζ(h) | 98 | 105 | 99 | 116 |
| PKD2(h) | 100 | 97 | 103 | 115 |
| PRAK(h) | 88 | 96 | 101 | 102 |
| PRK2(h) | 106 | 113 | 110 | 126 |
| ROCK-II(h) | 110 | 103 | 107 | 104 |
| ROCK-II(r) | 101 | 92 | 83 | 91 |
| Ros(h) | 79 | 108 | 117 | 105 |
| Rsk1(h) | 39 | 15 | 15 | 85 |
| Rsk1(r) | 37 | 7 | 5 | 67 |
| Rsk2(h) | 32 | 10 | 12 | 63 |
| Rsk3(h) | 33 | 5 | 5 | 25 |
| SAPK2a(h) | 108 | 92 | 92 | 93 |
| SAPK2b(h) | 104 | 119 | 114 | 99 |
| SAPK3(h) | 78 | 115 | 103 | 114 |
| SAPK4(h) | 101 | 104 | 102 | 102 |
| SGK(h) | 93 | 105 | 109 | 93 |
| Syk(h) | 86 | 101 | 105 | 109 |
| Tie2(h) | 110 | 109 | 96 | 107 |
| TrkB(h) | Fail | 98 | 105 | 106 |
| Yes(h) | 96 | 79 | 58 | 43 |
| ZAP-70(h) | 113 | 103 | 115 | 121 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I)

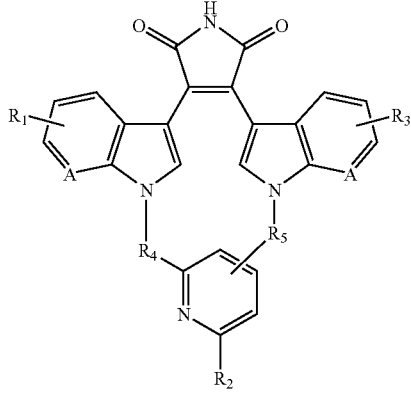

Formula (I)

wherein:

A is CH;

$R_1$ and $R_3$ are each selected from the group consisting of hydrogen, $C_{1-4}$alkyl, $C_{2-4}$alkenyl, $C_{1-4}$alkoxy, $C_{1-4}$alkylthio, halogen, trifluoromethyl, trifluoromethoxy, hydroxy, hydroxy($C_{1-4}$)alkyl, nitro, amino, ($C_{1-4}$)alkylamino, and di($C_{1-4}$)alkylamino;

$R_4$ and $R_5$ are each $C_{2-6}$alkylene optionally substituted with oxo, wherein the point of attachment for $R_5$ is meta or ortho relative to the $R_2$ substituted pyridine carbon ring atom of the compound of Formula (I);

$R_2$ is $C_{6-10}$aryl or $NR_aR_b$; wherein $C_{6-10}$aryl is optionally substituted with one, two or three substituents independently selected from the group consisting of $C_{1-4}$alkyl, $C_{1-4}$alkoxy, halogen, amino, ($C_{1-4}$)alkylamino, di($C_{1-4}$)alkylamino, and $C_{1-4}$alkoxycarbonyl;

$R_a$ and $R_b$ are each $C_{1-6}$alkyl; or, $R_a$ and $R_b$ are taken together with the atoms to which they are attached to form a 5, 6, 7 or 8 membered monocyclic ring; wherein said monocyclic ring optionally contains one additional oxygen, sulfur, NH, or N($C_{1-4}$alkyl);

and enantiomers, diastereomers, racemates, and pharmaceutically acceptable salts thereof.

2. The compound of claim 1, wherein $R_1$ and $R_3$ are each selected from the group consisting of hydrogen, methyl, methoxy, halogen, and hydroxy.

3. The compound of claim 2, wherein $R_1$ and $R_3$ are each hydrogen.

4. The compound of claim 1, wherein $R_4$ and $R_5$ are each $C_{3-4}$alkylene.

5. The compound of claim 4, wherein $R_4$ and $R_5$ are each n-propylene or n-butylene.

6. The compound of claim 1, wherein $R_2$ is $C_{6-10}$aryl or $NR_aR_b$; wherein $C_{6-10}$aryl is optionally substituted with one or two substituents independently selected from the group consisting of $C_{1-4}$alkyl and halogen.

7. The compound of claim 6, wherein $R_2$ is phenyl optionally substituted with one to two methyl substituents.

8. The compound of claim 7, wherein $R_2$ is phenyl optionally substituted with one methyl substituent.

9. The compound of claim 8, wherein $R_2$ is 4-methylphenyl.

10. The compound of claim 1, wherein $R_a$ and $R_b$ are each $C_{1-4}$alkyl; or $R_a$ and $R_b$ are taken together with the atoms to which they are attached to form a 5 to 6 membered monocyclic ring.

11. The compound of claim 10, wherein $R_a$ and $R_b$ are each $C_{1-2}$alkyl; or $R_a$ and $R_b$ are taken together with the atoms to which they are attached to form a 5-membered monocyclic ring.

12. A compound of Formula (Ia)

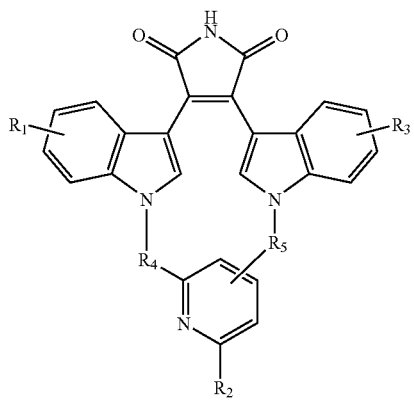

Formula (Ia)

wherein:

$R_1$ and $R_3$ are each selected from the group consisting of hydrogen, methyl, methoxy, halogen, and hydroxy;

$R_4$ and $R_5$ are each $C_{3-4}$alkylene, wherein the point of attachment for $R_5$ is meta or ortho relative to the $R_2$ substituted pyridine carbon ring atom of the compound of Formula (I);

$R_2$ is $C_{6-10}$aryl or $NR_aR_b$; wherein $C_{6-10}$aryl is optionally substituted with one, two or three substituents independently selected from the group consisting of $C_{1-4}$alkyl and halogen;

$R_a$ and $R_b$ are each $C_{1-4}$alkyl; or $R_a$ and $R_b$ are taken together with the atoms to which they are attached to form a 5 to 6 membered monocyclic ring;

and enantiomers, diastereomers, racemates, and pharmaceutically acceptable salts thereof.

13. The compound of claim 12, wherein $R_1$ and $R_3$ are each hydrogen.

14. The compound of claim 12, wherein:

$R_4$ and $R_5$ are each n-propylene or n-butylene;

$R_2$ is phenyl or $NR_aR_b$; wherein phenyl is optionally substituted with one to two methyl substituents; and $R_a$ and $R_b$ are each $C_{1-2}$alkyl; or $R_a$ and $R_b$ are taken together with the atoms to which they are attached to form a 5-membered monocyclic ring.

15. The compound of claim 12, wherein $R_2$ is 4-methylphenyl or $NR_aR_b$.

16. A compound of claim 1 selected from the group consisting of:

31-(dimethylamino)-5,15,25,32-tetraazaheptacyclo[28.2.2.1$^{5,12}$.1$^{18,25}$.0$^{6,11}$.0$^{13,17}$.0$^{19,24}$]hexatriaconta-1(32),6,8,10,12(36),13(17),18(35),19,21,23,30,33-dodecaene-14,16-dione, 20-(dimethylamino)-4,14,19,26-tetraazaheptacyclo[24.6.1.1$^{7,14}$.1$^{18,22}$.0$^{2,6}$.0$^{8,13}$.0$^{27,32}$]pentatriaconta-1(33),2(6),7(35),8,10,12,18(34),19,21,27,29,31-dodecaene-3,5-dione, 31-(dimethylamino)-5,15,25,30-tetraazaheptacyclo [27.2.2.1$^{5,12}$.1$^{18,25}$.0$^{6,11}$.0$^{13,17}$.0$^{19,24}$]pentatriaconta-1 (31),6,8,10,12(35),13(17),18(34),19,21,23,29,32- dodecaene-14,16-dione, 20-(4-methylphenyl)-4,14,19,26-tetraazaheptacyclo [24.6.1.1$^{7,14}$.1$^{18,22}$.0$^{2,6}$.0$^{8,13}$.0$^{27,32}$]pentatriaconta-1 (33),2(6),7(35),8,10,12,18(34),19,21,27,29,31-dode- caene-3,5-dione, 33-pyrrolidin-1-yl-6,16,26,32-tetraazaheptacyclo [29.2.2.1$^{6,13}$.1$^{19,26}$.0$^{7,12}$.0$^{14,18}$.0$^{20,25}$]heptatriaconta-1 (33),7,9,11,13(37),14(18),19(36),20,22,24,31,34- dodecaene-15,17-dione, 20-pyrrolidin-1-yl-4,14,19,26-tetraazaheptacyclo [24.6.1.1$^{7,14}$.1$^{18,22}$.0$^{2,6}$.0$^{8,13}$.0$^{27,32}$]pentatriaconta-1 (33),2(6),7(35),8,10,12,18(34),19,21,27,29,31-dode- caene-3,5-dione, and 31-pyrrolidin-1-yl-5,15,25,30-tetraazaheptacyclo [27.2.2.1$^{5,12}$.1$^{18,25}$.0$^{6,11}$.0$^{13,17}$0$^{19,24}$]pentatriaconta-1 (31),6,8,10,12(35),13(17),18(34),19,21,23,29,32- dodecaene-14,16-dione.

17. A pharmaceutical composition comprising the compound of claim 1 and a pharmaceutically acceptable carrier.

18. A pharmaceutical composition comprising the compound of claim 12 and a pharmaceutically acceptable carrier.

19. A process for synthesizing a compound of Formula (I):

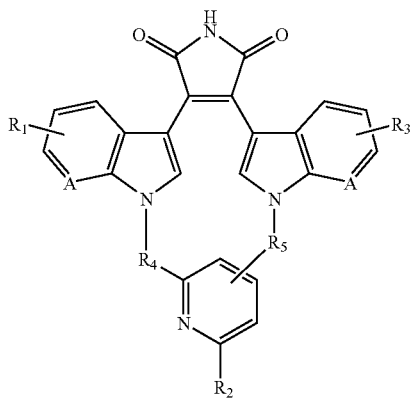

Formula (I)

wherein:

A is CH;

R$_1$ and R$_3$ are each selected from the group consisting of hydrogen, C$_{1-4}$alkyl, C$_{2-4}$alkenyl, C$_{1-4}$alkoxy, C$_{1-4}$alkylthio, halogen, trifluoromethyl, trifluoromethoxy, hydroxy, hydroxy(C$_{1-4}$)alkyl, nitro, amino, (C$_{1-4}$)alkylamino, and di(C$_{1-4}$)alkylamino;

R$_4$ and R$_5$ are each C$_{2-6}$alkylene optionally substituted with oxo, wherein the point of attachment for R5 is meta or ortho relative to the R$_2$ substituted pyridine carbon ring atom of the compound of Formula (I);

R$_2$ is C$_{6-10}$aryl or NR$_a$R$_b$; wherein C$_{6-10}$aryl is optionally substituted with one, two or three substituents independently selected from the group consisting of C$_{1-4}$alky, C$_{1-4}$alkoxy, halogen, amino, (C$_{1-4}$)alkylamino, di(C$_{1-4}$) alkylamino, and C$_{1-4}$alkoxycarbonyl;

R$_a$ and R$_b$ are each C$_{1-6}$alkyl; or, R$_a$ and R$_b$ are taken together with the atoms to which they are attached to form a 5, 6, 7 or 8 membered monocyclic ring; wherein said monocyclic ring optionally contains one additional oxygen, sulfur, NH, or N(C$_{1-4}$alkyl);

comprising the steps of:

Step A. reacting a compound of Formula A1 in the presence of a base with a compound of Formula A2 to provide a compound of Formula A3:

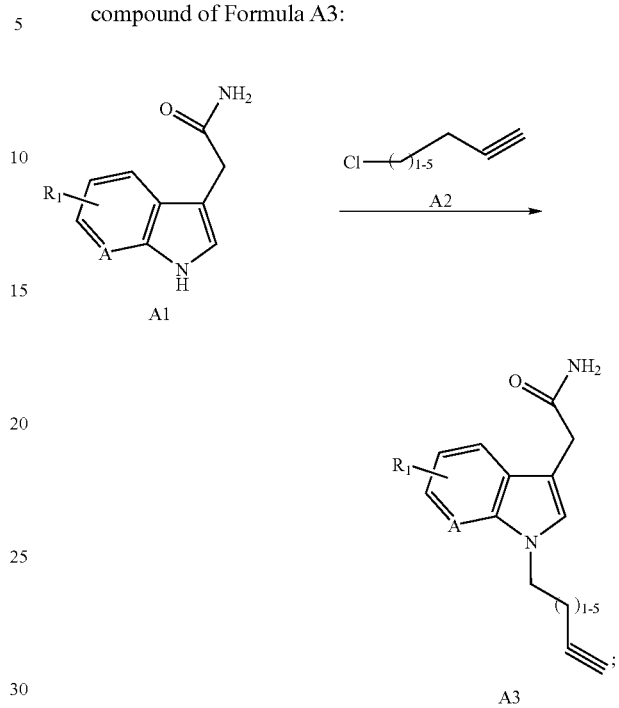

Step B. reacting a compound of Formula A4 in the presence of a base with the compound of Formula A2 to provide a compound of Formula A5:

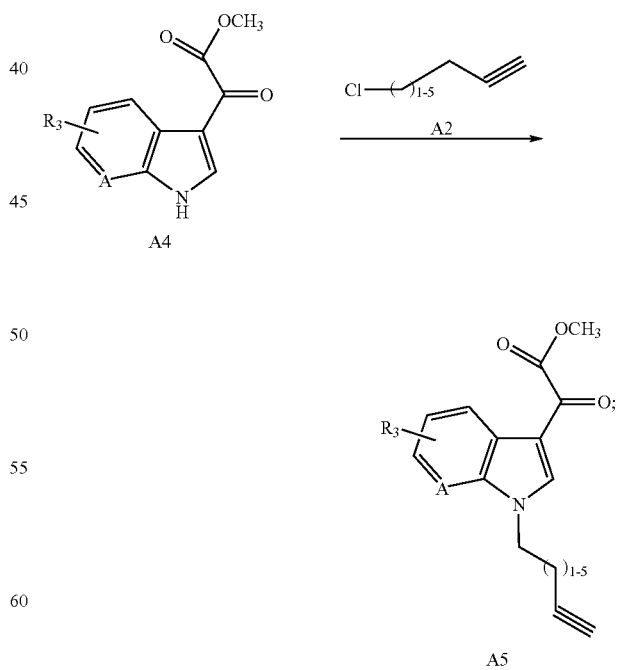

Step C. reacting the compound of Formula A3 in the presence of a base with the compound of Formula A5 to provide a compound of Formula A6:

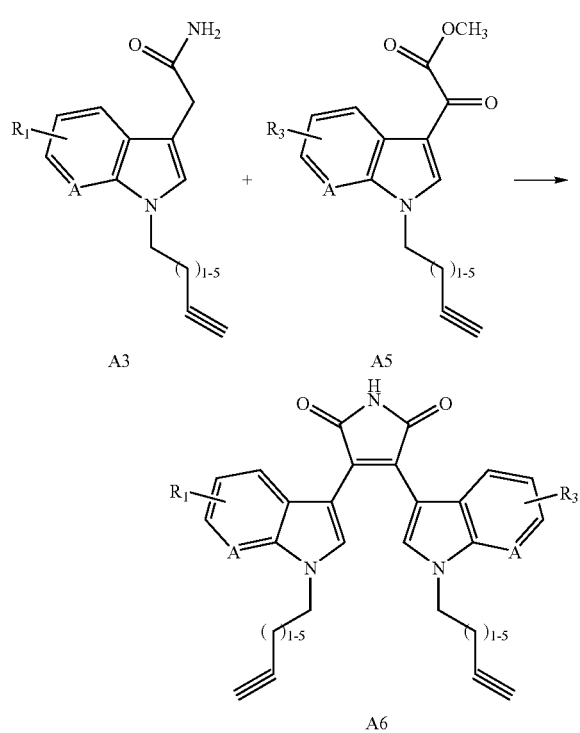

and

Step D. reacting the compound of Formula A6 with the compound of Formula A7 in the presence of a cobalt catalyst to provide a compound of Formula A8, representative of a compound of Formula (I):

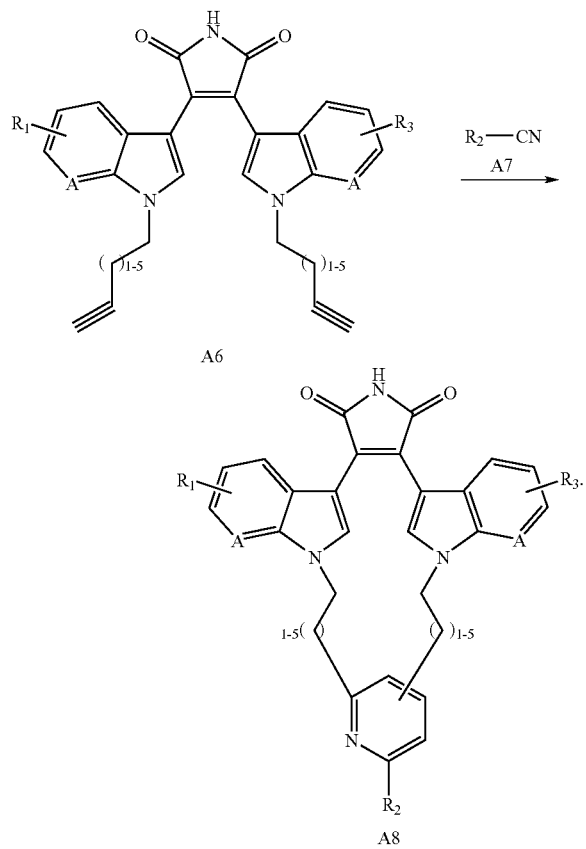

20. The process of claim 19, wherein the compound of Formula A6 is present in a range of from about 1 molar equivalents to about 10 molar equivalents.

21. The process of claim 20, wherein the compound of Formula A6 is present in a range of from about 4 molar equivalents to about 8 molar equivalents.

22. The process of claim 19, wherein the cobalt catalyst is $CpCo(CO)_2$.

23. The process of claim 19, wherein the cobalt catalyst is present in a range of from about 0.1 molar equivalents to about 1 molar equivalent.

24. The process of claim 23, wherein the cobalt catalyst is present in a range of from about 0.2 molar equivalents to about 0.5 molar equivalents.

25. The process of claim 19, wherein the cobalt catalyst is present in an aprotic organic solvent.

26. The process of claim 25, wherein the aprotic organic solvent is selected from toluene, 1,4-dioxane, or dimethoxyethane.

27. The process of claim 26, wherein the aprotic organic solvent is selected from 1,4-dioxane or dimethoxyethane.

28. The process of claim 19, wherein the reaction of the compound of Formula A6 with the compound of Formula A7 is optionally conducted in the presence of triphenylphosphine, is optionally at an elevated temperature and is optionally under an inert atmosphere.

29. The process of claim 28, wherein the temperature is from about 60° C. to about 140° C.

30. The process of claim 29, wherein the temperature is from about 80° C. to about 110° C.

31. The process of claim 28, wherein the inert atmosphere is Argon.

32. The process of claim 28, wherein triphenylphosphine is present in a range of from about 0.1 molar equivalents to about 1 molar equivalent.

33. The process of claim 32, wherein triphenylphosphine is present in a range of from about 0.2 molar equivalents to about 0.5 molar equivalents.

34. The process of claim 19, wherein the compound of Formula (I) is selected from a compound wherein:

$R_1$ and $R_3$ are each selected from the group consisting of hydrogen, methyl, methoxy, halogen, and hydroxy;

$R_4$ and $R_5$ are each $C_{3-4}$alkylene;

$R_2$ is $C_{6-10}$aryl or $NR_aR_b$; wherein $C_{6-10}$aryl is optionally substituted with one or two substituents independently selected from the group consisting of $C_{1-4}$alkyl and halogen; and $R_a$ and $R_b$ are each $C_{1-4}$alkyl; or $R_a$ and $R_b$ are taken together with the atoms to which they are attached to form a 5 to 6 membered monocyclic ring.

* * * * *